(12) United States Patent
Sandig et al.

(10) Patent No.: US 11,999,975 B2
(45) Date of Patent: Jun. 4, 2024

(54) METHOD FOR PURIFYING AN ENVELOPED VIRUS

(71) Applicant: ProBioGen AG, Berlin (DE)

(72) Inventors: Volker Sandig, Berlin (DE); Michael Mühle, Berlin (DE); Sven Krügener, Berlin (DE)

(73) Assignee: ProBioGen AG, Berlin (DE)

( * ) Notice: Subject to any disclaimer, the term of this patent is extended or adjusted under 35 U.S.C. 154(b) by 612 days.

(21) Appl. No.: 17/256,158

(22) PCT Filed: Jun. 27, 2019

(86) PCT No.: PCT/EP2019/067216
§ 371 (c)(1),
(2) Date: Dec. 24, 2020

(87) PCT Pub. No.: WO2020/007715
PCT Pub. Date: Jan. 9, 2020

(65) Prior Publication Data
US 2022/0267738 A1    Aug. 25, 2022

(30) Foreign Application Priority Data
Jul. 4, 2018    (EP) .................... 18181748

(51) Int. Cl.
| | |
|---|---|
| *C07K 1/22* | (2006.01) |
| *B01D 15/32* | (2006.01) |
| *B01D 15/36* | (2006.01) |
| *B01D 15/38* | (2006.01) |
| *C07K 1/16* | (2006.01) |
| *C07K 1/18* | (2006.01) |
| *C07K 1/36* | (2006.01) |
| *C12N 7/00* | (2006.01) |
| *C12N 15/113* | (2010.01) |

(52) U.S. Cl.
CPC .............. *C12N 7/00* (2013.01); *B01D 15/327* (2013.01); *B01D 15/361* (2013.01); *B01D 15/3847* (2013.01); *C12N 15/113* (2013.01); *C12N 2710/24151* (2013.01); *C12N 2760/18151* (2013.01)

(58) Field of Classification Search
CPC . C07K 1/22; C07K 1/16; C07K 1/165; C07K 1/18; C07K 1/36
See application file for complete search history.

(56) References Cited

U.S. PATENT DOCUMENTS

| | | |
|---|---|---|
| 2009/0042274 A1 | 2/2009 | Shinichi |
| 2010/0112001 A1 | 5/2010 | Djurup |
| 2010/0119552 A1 | 5/2010 | Hansen |
| 2013/0288339 A1 | 10/2013 | Post Hansen et al. |
| 2015/0064768 A1 | 3/2015 | Kapre |

FOREIGN PATENT DOCUMENTS

| | | |
|---|---|---|
| JP | 2007-238479 A | 9/2007 |
| JP | 2007238479 A | 9/2007 |
| JP | 2010-533001 | 10/2010 |
| JP | 2014-516515 | 7/2014 |
| WO | WO 2009/009876 A1 | 1/2009 |
| WO | WO 2012/145837 A1 | 11/2012 |
| WO | WO2013067301 * | 5/2013 |
| WO | WO2013/154928 | 10/2013 |
| WO | WO2016/041844 | 3/2016 |

OTHER PUBLICATIONS

Hirano et al., Interaction of arginine with Capto MMC in multimodal chromatography, J Chromat. A, 2014, 58-66, v. 1338.
Vajda, et al., Mono- and polyprotic buffer systems in anion exchangechromatography of influenza virus particles, J Chromat. A, 2016, 73-80, v. 1448.
Hara, Taiki, Notice of reasons for refusal, JP Patent Office, "dispatch date" Feb. 14, 2023.
Stoyanov, B., International Search Report, European Patent Office, PCT/EP2019/067216, dated Aug. 27, 2019.
Stoyanov, B., Written Opinion, European Patent Office, PCT/EP2019/067216, dated Aug. 27, 2019.

* cited by examiner

*Primary Examiner* — Barry A Chestnut
(74) *Attorney, Agent, or Firm* — Laurence J. Hyman; Hyman IP Law

(57) ABSTRACT

The present invention relates to a method for purifying an enveloped virus. The present invention further relates to an enveloped virus or a plurality of enveloped viruses obtainable by said method.

7 Claims, 4 Drawing Sheets
Specification includes a Sequence Listing.

METHOD FOR PURIFYING AN ENVELOPED VIRUS

The present invention relates to a method for purifying an enveloped virus. The present invention further relates to an enveloped virus or a plurality of enveloped viruses obtainable by said method.

BACKGROUND OF THE INVENTION

Beyond monoclonal antibodies today there is a great promise for novel biopharmaceutical products based on virus particles. These virus particles are applicable for gene therapy or for vaccination. The broad spectrum of applications, especially for treatment or prevention of cancer and infectious diseases, in combination with expanding medical markets, is driving the efforts to improve the manufacturing processes for gene therapy vectors and viral vaccines.

The use of well characterized animal cell lines and scalable production systems allowed for major improvements of native and recombinant virus titer and product quality. However, much less effort has been put to downstream purification processes for virus particles.

Contaminants, either process-related (e.g., bovine serum albumin, extractables, nuclease, leachables) or product-related (e.g., host cell proteins, host cell DNA, proteoglycans, and glycosaminoglycans) must, as a rule, be removed by purification processes. As upstream titers keep improving, downstream processing (DSP) of viruses becomes a critical bottleneck. Beside particle size and heterogeneity, isoelectric point (pI) and surface hydrophobicity, the lability of the virus plays an important role in the design of purification processes of live viruses. This is particularly true for enveloped viruses, as the physicochemical properties of viral envelopes represent a challenge for cost-efficient industrial virus manufacturing.

Many DNA- and RNA viruses have a viral envelope. The lipid bilayer envelope covers their protein capsids and is derived from portions of the host cell membrane, which includes viral glycoproteins. In order to evade the immune system, viruses can change surface proteins in a short time. Moreover, the envelope of these viruses is relatively sensitive to heat, detergents and desiccation, which leads to limited survival of enveloped viruses outside host environments. Enveloped viruses are more likely to be denatured than non-enveloped viruses and typically must transfer/be transferred directly from host to host.

Still, enveloped viruses are used as live attenuated vaccines. They induce a broader immune response than inactivated virions or purified subunits.

Some enveloped viruses are even used as vectored vaccines e.g. pox viruses, alphaviruses, flaviviruses, paramyxoviruxes and herpes viruses. In this case, the enveloped virus is used to carry antigens of another virus or tumor antigens for expression in the recipient. Other enveloped viruses used as vectors for gene therapy including retroviruses, pox viruses and herpes viruses.

Clearly, the challenges lie in the gentle downstream processing (DSP) of life enveloped viruses to maintain virus infectivity, which is essential, e.g. for gene therapy applications, viral vector vaccines, or oncolytic viruses.

Corresponding processes used in the art to purify enveloped viruses are often limited in their ability to be transferred to large-scale, are related to significant yield losses or do not meet the level of purity required for pharmaceutical products manufactured with continuous cell lines.

A large number of viruses-based vaccines is generated on finite cultures of primary cells including primary Chicken Embryo Fibroblasts (CEF). Due to the extensive experience with vaccines derived from primary cells and their limited life span vaccines produced on primary CEF cells are generally recognised as save and less stringent requirement with respect to the level of host cell DNA or host cell protein apply. However, because CEF cells have to be generated from embryonated eggs they pose a potential risk of contaminating infectious agents despite egg production in specific pathogen free (SPF) farms. Costly manufacture and expensive biosafety testing of each produced vaccine batch has motivated the industry to favour continuous cell lines Immortal cells can be banked, characterized at the cell bank level and used for multiple vaccine batches produced that require less extensive testing for the individual batch. Moreover, continuous cell lines permit the incorporation of helper genes to support live attenuated viruses and live but replication incompetent viral vectors.

One example of such vector is the Modified Vaccinia Ankara (MVA) virus, a highly attenuated vaccinia virus, incapable of replicating in human cells that serves as an important vaccine vector to carry antigens of unrelated viruses or specific tumour antigens. Vaccinia is the largest DNA virus. Another example is the Newcastle disease (ND) virus, an avian paramyxovirus, that has shown potential to replicate in human tumours and can serve as oncolytic agent to kill tumour cells and mount a potent antitumor immune response. Both viruses historically have been propagated on CEF cells.

Other viral vectors applied as vaccines or gene therapy delivery vehicles such as Sendai virus (another Paramyxovirus), Venezuelan encephalitis virus replicon vectors, derived from the respective alphavirus, Yellow fever virus (YF17D), a Flavivirus, are propagated on continuous cell lines. Lentivirus vectors used for permanent gene modification are produced by transient transfection and require permanent cell lines as a substrate.

Most immortal cell lines, in particular those that have been adapted to growth in suspension, have gained the potential to grow in immune compromised animals (newborn nude mice) when injected at a high cell dose. In rare cases, tumour formation is also found after injection of cellular DNA.

Such cell lines could potentially transfer the immortalizing/transforming agent (nucleic acid or protein) to a vaccine recipient. Hence stringent requirements are imposed with respect to purity of viruses and viral vectors produced on immortal cell lines.

To achieve such low level of host cell contaminants, new and improved methods for purification are needed. The aim is to improve virus yield on the one hand and meet regulatory requirements on the other hand.

Depending on the type of enveloped virus used in the manufacturing of vaccines or gene therapy, vectors can be purified in different ways. Traditionally, purification of enveloped viruses has been carried out based on methods separating molecules by means of their size and specific density differences. Density gradient centrifugation is state-of-the-art in viral downstream purification processes. For example, sucrose, iododixanol, or caesium chloride gradients are generally used to purify limited amounts of virus for preclinical studies. Additionally, for further removal of host cell DNA and other host cell contaminants, secondary methods such as ultrafiltration or nuclease treatments (e.g. Benzonase) are used.

The poor scalability and economics of these processes and mentioned higher regulatory requirements regarding the purity of virus preparations used for medical applications led to the development of new technologies based on chromatographic methods. These methods are well-known and established and have been widely used in the downstream processing of virus particles. Most common for chromatographic concentration and purification of virus particles are affinity, ion exchange, hydrophobic interaction and size exclusion chromatography.

To illustrate a specific approach to counter the host cell DNA issue, the vaccinia virus is used as an example (without limiting this approach to vaccinia virus only): The three surface proteins A27L, D8L, and H3L of vaccinia virus have been reported to mediate vaccinia virus interaction with cell surface heparin sulphate. Therefore, heparin and heparin sulphate where used in affinity chromatography applications for vaccinia purification resulting in a DNA depletion of 77% with a yield loss of 37% (Wolff et al. Biotechnology and Bioengineering, 105 (4), 2010, 761-769).

U.S. Pat. No. 9,273,289 B2 uses a combination of chaotropic agents and silicate filtration for purification to recover 52% of the infectious units and deplete 17% of host cell DNA.

For efficient purification of enveloped virus particles, e.g. vaccinia virus particles, from an infected cell line, some significant challenges have to overcome. The described methods often do not meet the level of purity required for pharmaceutical products manufactured with continuous cells. Conditions (like salt concentrations and pH) required for separation of components often cause virus aggregation or virus inactivation, in particular for sensitive enveloped viruses. Pseudo-affinity chromatography may overcome some hurdles but is limited to specific viruses.

Thus, there is a need for new methods for the purification of enveloped viruses with high activity for a human prophylactic or therapeutic product. Said new methods should be fast, cost-efficient, universal, robust, and industrially scalable. In addition, said methods should allow the preparation of enveloped viruses with high yield and purity. In particular, the preparation of enveloped viruses should comprise as less as possible host cell-derived nucleic acids such as DNA and/or RNA as well as host cell-derived proteins. Multimodal chromatography or mixed-mode chromatography (MMC) is a technique which is used for the separation of various biomolecules and refers to a chromatographic method that utilizes more than one type of partitioning principle for the separation. Technologies for antibody purification via MMC are known in art. Among other purposes, MMC is used to remove viruses from protein preparations. In this case, protein solutions are passed through the mixed mode carrier in flow-through mode, whereas contaminants including viruses remain tightly bound to the resin, thereby purifying the protein.

The inventors of the present patent application surprisingly established, for the first time, a hydrophobic ionic exchange mixed-mode chromatography for the purification of enveloped viruses. This is a fully scalable and reproducible process. Said process allows the purification of enveloped viruses with high yield and purity. In addition, the inventors of the present patent application discovered that the presence of arginine in the elution buffer further allows to increase virus yield and purity and can even compensate for high salt concentrations usually used for elution. The recovery of large amounts of enveloped viruses is extremely surprising as in the art arginine is used to inactivate enveloped viruses (EP2350271 B1). The method for virus purification of the present invention uses a mixed-mode chromatography in bind-elute-mode which is suitable to overcome actual shortcomings in the purification of enveloped viruses (e.g. in terms of purity, speed, recovery, universality, robustness and/or scalability). Said method is suitable to purify any enveloped virus from virus preparations. The virus preparations obtained in the described process fulfil the stringent guidelines of the regulatory authorities.

SUMMARY OF THE INVENTION

In a first aspect, the present invention relates to a method for purifying an enveloped virus comprising the steps of:
(i) binding an enveloped virus comprised in a preparation to a mixed mode chromatography carrier, and
(ii) eluting the enveloped virus from the mixed mode chromatography carrier,
wherein the mixed mode chromatography carrier is a hydrophobic ion exchange chromatography carrier.

In a second aspect, the present invention relates to an enveloped virus or a plurality of enveloped viruses obtainable by the method of the first aspect.

In a third aspect, the present invention relates to the enveloped virus or the plurality of enveloped viruses of the second aspect for use in medicine.

In a fourth aspect, the present invention relates to an elution buffer comprising arginine.

In a fifth aspect, the present invention relates to the use of a buffer comprising arginine to elute an enveloped virus.

In a sixth aspect, the present invention relates to a kit for purifying an enveloped virus comprising:
(i) a mixed mode chromatography carrier, wherein the mixed mode chromatography carrier is a hydrophobic ion exchange chromatography carrier,
(ii) one or more of the following buffers: equilibration buffer, washing buffer, and elution buffer, and
(iii) optionally a nuclease.

This summary of the invention does not necessarily describe all features of the present invention. Other embodiments will become apparent from a review of the ensuing detailed description.

DETAILED DESCRIPTION OF THE INVENTION

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention. In the event of a conflict between the definitions or teachings of such incorporated references and definitions or teachings recited in the present specification, the text of the present specification takes precedence.

The term "comprise" or variations such as "comprises" or "comprising" according to the present invention means the inclusion of a stated integer or group of integers but not the exclusion of any other integer or group of integers. The term "consisting essentially of" according to the present invention means the inclusion of a stated integer or group of integers, while excluding modifications or other integers which would materially affect or alter the stated integer. The term "consisting of" or variations such as "consists of" according to the present invention means the inclusion of a stated integer or group of integers and the exclusion of any other integer or group of integers.

The terms "a" and "an" and "the" and similar reference used in the context of describing the invention (especially in the context of the claims) are to be construed to cover both the singular and the plural, unless otherwise indicated herein or clearly contradicted by context.

The term "about", as used herein when referring to a measurable value, such as an amount or concentration of a compound or agent of this invention, pH, time, temperature, and the like, is meant to encompass the indicated value and variations of 20%, 10%, 5%, 1%, 0.5%, or even 0.1% of the indicated value.

The term "virus", as used herein, refers to a small agent that replicates only inside living cells of other organisms. It may also be cultivated in cell culture. Viruses can infect all types of life forms, from animals and plants to microorganisms, including bacteria and archaea. While not inside an infected cell or in the process of infecting a cell, viruses exist in the form of independent particles. These viral particles, also known as virions, consist of two or three parts: (i) the genetic material made from either DNA or RNA, long molecules that carry genetic information, (ii) a protein coat, called the capsid, which surrounds and protects the genetic material, and in some cases (iii) an envelope of lipids that surrounds the protein coat when they are outside a cell. The shapes of these virus particles range from simple helical and icosahedral forms for some virus species to more complex structures for others. Thus, the term "virus", as used herein, also encompasses viral particles, particularly infectious particles.

The term "enveloped virus", as used herein, refers to a virus having an viral envelope covering its protective protein capsid. The envelopes typically are derived from portions of the host cell membranes (phospholipids and proteins), but include some (viral) glycostructures such as glycoproteins and/or glycooligopeptides. Functionally, viral envelopes help viruses to enter host cells and may help them to avoid the host immune system. (Viral) glycostructures such as glycoproteins and/or glycooligopeptides on the surface of the envelopes serve to identify and bind to receptor sites on the host's membrane. The viral envelope then fuses with the host's membrane, allowing the capsid and viral genome to enter and infect the host. The Modified Vaccinia Ankara (MVA) virus and the New Castle Disease Virus (NDV) are enveloped viruses. The term "enveloped virus", as used herein, also encompasses enveloped virus particles, particularly infectious enveloped virus particles.

The term "Modified Vaccinia Ankara (MVA) virus", as used herein, refers to a highly attenuated strain of vaccinia derived from the Ankara strain and developed for use as a vaccine and vaccine adjuvant. The original MVA virus was isolated from the wild-type Ankara strain by successive passage through chicken embryonic cells. Treated thus, it lost about 15% of the genome of wild-type vaccinia including its ability to replicate efficiently in primate (including human) cells. The MVA virus belongs to the class of enveloped viruses.

The term "New castle disease (ND) virus", as used herein, refers to a virus commonly known to cause a bird disease affecting many domestic and wild avian species. The virus is transmissible to humans. Exposure of humans to infected birds (for example in poultry processing plants) can cause mild conjunctivitis and influenza-like symptoms, but the ND virus otherwise poses no hazard to human health. Interest in the use of the ND virus as an anticancer agent has arisen from the ability of the ND virus to selectively kill human tumor cells with limited toxicity to normal cells. The ND virus belongs to the class of enveloped viruses.

The term "purified virus, particularly enveloped virus", as used herein, refers to a virus, particularly enveloped virus, that has been isolated under conditions that reduce or eliminate the presence of contaminants, including native material/(non-viral) intracellular substances/components, e.g. cells, cellular debris, cellular remnants, cellular proteins, cellular lipids, and/or cellular nucleic acids, such as DNA molecules and/or RNA molecules, from which the virus, in particularly enveloped virus, is obtained. The contaminants further include (non-viral) extracellular substances/components, e.g. medium additives (used in cell cultivation and virus production). Non-viral intracellular and non-viral extracellular substances may also be designated as virus unrelated material. The contaminants also include viral substances/components (excluding the (intact) virus which is desired), e.g. incomplete virus particles and adventitious viruses. Preferably, the contaminants include native material/(non-viral) intracellular substances and/or (non-viral) extracellular substances.

The purified virus, particularly enveloped virus, is preferably substantially free of contaminants, e.g. cellular components and/or culture components. The term "substantially free", as used herein, means that preferably at least 50%, more preferably at least 90%, even more preferably at least 95%, and most preferably at least 99% or 100% of the contaminants, e.g. at least 50, 60, 70, 80, 90, 91, 92, 93, 94, 95, 96, 97, 98, 99% or 100%, of the contaminants, e.g. comprised in the virus producing cell and/or its cell culture medium, are removed. In other words, a purified virus, in particular enveloped virus, which is substantially free of contaminants is preferably at least 50% pure, more preferably at least 90% pure, even more preferably at least 95% pure, and most preferably at least 99% or 100% pure, e.g. at least 50, 60, 70, 80, 90, 91, 92, 93, 94, 95, 96, 97, 98, 99% or 100% pure.

The term "(percent) purity", as used herein, is intended to mean the purity achieved when the virus, in particular enveloped virus, is conveyed through a purification step, compared to the purity of the virus in the preparation/sample prior to the purification step. Achieving an increase in purity entails obtaining a virus, in particular enveloped virus, with a reduced level of contaminants (in proportion to the virus, in particular enveloped virus), when a preparation/sample is compared before and after a purification step. Percentages within the meaning of purity as defined above include, without limitation, preferably at least 50%, more preferably at least 90%, even more preferably at least 95%, and most preferably at least 99% or 100%, e.g. at least 50, 60, 70, 80, 90, 91, 92, 93, 94, 95, 96, 97, 98, 99%, or 100%.

Purity can be evaluated by chromatography, gel electrophoresis, immunoassay, composition analysis, biological assay, and other methods known in the art. The purity can also be expressed as specific impurity, which is the amount of each impurity per dose (e.g. ng nucleic acids/dose). The preparation comprising an enveloped virus, as purified herein, preferably comprises ≤10 ng nucleic acids/dose, e.g. 0,≤0.1, 0.2, 0.3, 0.4, 0.5, 0.6, 0.7, 0.8, 0.9, 1.0, 2.0, 3.0, 4.0, 5.0, 6.0, 7.0, 8.0, 9.0, or 10.0 ng nucleic acid/dose. The nucleic acids encompass DNA and/or RNA molecules.

The term "purification" of a virus, particularly an enveloped virus, as used herein, refers to the removal of contaminants or measurable reduction of the level of contaminants in the virus, particularly enveloped virus, preparation.

The term "virus activity", as used herein, is defined as virions that are either (i) infectious in at least one cell type, (ii) immunogenic in animals such as humans, or (iii) both infectious and immunogenic. An "active virus", in particularly "active enveloped virus", is preferably one that is either infectious in at least one cell type or immunogenic in animals such as humans or both. Preferably, the virus activity is preserved during purification. In particular, the virus activity is preserved during purification such that at least 30%, preferably at least 40%, more preferably at least 50%, even more preferably at least 80%, and most preferably at least 90% or more, e.g. at least 30, 40, 50, 60, 70, 80, 90, 91, 92, 93, 94, 95, 96, 97, 98, 99%, or 100%, of the initial 50% Tissue culture infective Dose ($TCID_{50}$) is retained during purification. 50% Tissue culture Infective Dose ($TCID_{50}$) is the measure of infectious virus titer. This endpoint dilution assay quantifies the amount of virus required to kill 50% of infected hosts or to produce a cytopathic effect in 50% of inoculated tissue culture cells. Two methods commonly used to calculate TCID50 are: Spearman-Karber and Reed-Muench method. Alternative method to determine virus activity are known to the person skilled in the art.

The term "virus vaccine, in particular enveloped virus vaccine", as used herein, refers to an agent that can be used to induce an immune response or to elicit protective immunity in a recipient, e.g. human or animal recipient. To be effective, a virus vaccine can elicit immunity in a portion of the immunized population, as some individuals may fail to mount a robust or protective immune response or, in some cases, any immune response. This inability may stem from the genetic background of the recipient or because of an immunodeficiency condition (either acquired or congenital) or immunosuppression (e.g., due to treatment with chemotherapy or use of immunosuppressive drugs). Virus vaccine efficacy can be established in animal models.

The term "vaccination", as used herein, means that a specific immunity against viral antigens is induced in a recipient, e.g. human or animal recipient, by mucosal or transdermal exposure with an attenuated infectious virus or by injection of an inactivated form of said virus. After the administration of the vaccine into the body of the recipient, the epitopes are expressed and are presented to the immune system and a specific immune response against these epitopes may be induced. The recipient is, thus, immunized against the molecule containing the epitope.

The term "cell culture", as used herein, refers to a process by which cells are grown under controlled conditions, generally outside of their natural environment. In practice, the term "cell culture" refers to the culturing of cells derived from multicellular organisms, e.g. human or animal cells. In a virus cell culture, the cells are hosts for the viruses. After virus cell culture, a cell suspension comprising the virus, in particular enveloped virus, in an enriched amount is achieved. The virus may be inside the cell and/or outside the cell (i.e. in the cell surrounding medium).

The term "primary cell culture", as used herein, refers to a cell culture that is derived directly from excised, normal human or animal tissue and cultured either as an explant culture or following dissociation into a single cell suspension by enzyme digestion. Such a culture is initially heterogeneous but later become dominated by fibroblasts. The preparation of primary cultures is labor intensive and they can be maintained in vitro only for a limited period of time. During their limited lifespan, primary cells usually retain many of the differentiated characteristics of the cell in vivo.

The term "continuous cell culture" (or "immortalized cell culture"), as used herein, describes cells that have been propagated in culture since the establishment of a primary culture, and they are able to grow and survive beyond the natural limit of senescence. Such surviving cells are considered as immortal. In other words, the term "continuous cell culture", as used herein, refers to a culture comprising a single cell type that can be serially propagated in culture for prolonged periods. It has an indefinite lifespan. Continuous or immortalized cell lines can be created, e.g. by inducing of oncogenes or by loss of tumor suppressor genes. Viruses may be propagated in a continuous or immortalized cell culture.

The term "contaminants", as used herein, encompasses (non-viral) intracellular substances, e.g. cells, cellular debris, cellular remnants, cellular proteins, cellular lipids, and/or cellular nucleic acids, such as DNA molecules and/or RNA molecules, from which the virus, in particularly enveloped virus, is obtained. The contaminants further include (non-viral) extracellular substances, e.g. medium additives (used in cell cultivation and virus production). Non-viral intracellular and non-viral extracellular substances may also be designated as virus unrelated material. The contaminants also include viral substances (excluding the (intact) virus which is desired), e.g. incomplete virus particles and adventitious viruses. In addition, the contaminants include process-related impurities such as impurities that arise from or during separation and/or purification processes.

Preferably, the contaminants include (non-viral) intracellular substances, (non-viral) extracellular substances, and/or viral substances (excluding the (intact) virus which is desired). More preferably, the contaminants include (non-viral) intracellular substances and/or (non-viral) extracellular substances.

In this respect, it should be noted that with the dynamic binding capacity of the respective MMC, a minimum of 50,000 doses of $1 \times 10^8$ MVA virus particles per capture cycle can be provided from a 10 l chromatography column with the method of the present invention. More preferably, more than 400 000 doses of $1 \times 10^8$ virus particles per capture cycle can be provided from a 10 l chromatography column with the method of the present invention. The preparation comprising an enveloped virus, as purified herein, preferably comprises ≤40 ng nucleic acids/dose, e.g. 0,≤0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 ng nucleic acid/dose. The nucleic acids encompass DNA and/or RNA molecules.

The term "preparation comprising an enveloped virus", as used herein, refers to any composition containing an enveloped virus that is desired to be purified. In particular, the preparation provided in the method of the present invention refers to a preparation comprising an enveloped virus that is desired to be purified from one or more contaminants such as, but not limited to, cellular proteins, cellular nucleic acids, cellular lipids, various cell culture media components and additives, incomplete virus particles, and/or adventitious viruses. The preparation comprising an enveloped virus provided in the method of the present invention may be an impure, unpurified or a partially purified preparation. An impure, unpurified preparation may be a cell suspension comprising an enveloped virus (the enveloped virus may be inside and/or outside the cell) or a cell lysate comprising an enveloped virus. The partially purified preparation comes from an unpurified preparation, e.g. cell suspension comprising an enveloped virus or a cell lysate comprising an enveloped virus, that has been further processed (e.g. by at least one of filtration, centrifugation, and fractionation step or by any combination thereof).

Alternatively, the preparation comprising an enveloped virus can be from any of the following steps in a manufacturing process: after virus growth (e.g. cell suspension comprising an enveloped virus), after cell lysis (e.g. cell lysate comprising an enveloped virus), or after one or more virus pre-purification/pre-treatment step(s) (e.g. a clarified virus preparation comprising an enveloped virus), e.g. filtration, centrifugation, and/or fractionation.

Preferably, the preparation comprising an enveloped virus provided in the method of the present invention is a cell suspension comprising an enveloped virus, a cell lysate comprising an enveloped virus, or a clarified virus preparation comprising an enveloped virus.

It is particularly preferred that the preparation comprising an enveloped virus provided in the method of the present invention is an aqueous preparation, in particular an aqueous suspension.

The term "heterologous nucleic acid sequence", as used herein, refers to a nucleic acid sequence that is normally not found intimately associated with the virus, particularly enveloped virus, in nature. A virus comprising a heterologous nucleic acid sequence may also be designated as recombinant virus. The heterologous nucleic acid sequence is preferably selected from a sequence coding for (i) an antigen, particularly an epitope of an antigen, (ii) a diagnostic compound, and (iii) a therapeutic compound.

The term "mixed mode chromatography carrier", as used herein, refers to a solid phase chromatographic carrier that employs a combination of two or more chemical mechanisms in order to achieve separation of two or more components, such as contaminants, e.g. proteins, nucleic acids such as DNA and/or RNA molecules, and viruses, in a mixture. Examples include, but are not limited to, chromatographic carrier that exploit combinations of cation exchange (i.e. in which the carrier is anionic), anion exchange (i.e. in which the carrier is cationic), hydrophobic interaction, hydrophilic interaction, hydrogen bonding, pi-pi bonding, and metal affinity. The solid phase can be a porous particle, non-porous particle, membrane, or monolith. In the method of the present invention, the mixed mode chromatography carrier is a hydrophobic ion exchange chromatography carrier, e.g. a hydrophobic cation exchange chromatography carrier or a hydrophobic anion exchange chromatography carrier, preferably a hydrophobic cation exchange chromatography carrier.

The term "hydrophobic interaction chromatography (HIC) carrier", as used herein, refers to the separation of components based on hydrophobic interactions with the stationary phase. Therefore, the elution order in HIC enables components to be ranked on the basis of their relative hydrophobicity. HIC employs non-denaturing conditions, does not require the use of organic solvents or high temperatures, and separations are carried out at physiological pH, which allows the preservation of virus structure when used in virus purification processes.

The term "ion exchange chromatography carrier", as used herein, refers to a chromatography carrier which allows the separation of ionisable molecules based on their total charge. The ion exchange chromatography carrier may be an "anion exchange chromatography carrier" or a "cation exchange chromatography carrier". An anion exchange chromatography carrier is a solid phase chromatographic carrier that has an affinity for molecules having net positive surface charges in order to achieve separation of components. A cation exchange chromatography carrier is a solid phase chromatographic carrier that has an affinity for molecules having net negative surface charges in order to achieve separation of components. The solid phase can be a porous particle, non-porous particle, membrane, or monolith.

The term "ligand", as used herein, refers to a specific binding structure attached to the mixed mode chromatography carrier, in particular hydrophobic interaction chromatography (HIC) carrier, which allows purification of the enveloped virus by binding said virus.

The term "washing buffer", as used herein, refers to a solution used to remove contaminants from a mixed mode chromatography carrier, in particular hydrophobic ion exchange chromatography carrier, to which the enveloped virus is bound. Due to the washing buffer, the enveloped virus bound to the carrier is purified.

The term "elution buffer", as used herein, refers to a solution used to elute or dissociate the enveloped virus from the mixed mode chromatography carrier, in particular hydrophobic ion exchange chromatography carrier, to which the enveloped virus is bound. In other words, the elution buffer is used to rescue the enveloped virus from the mixed mode chromatography carrier.

The term "virus clarification", as used herein, refers to any technique which allows to separate harvested infected cell culture material from solid components (cells and cell debris). This may be achieved, for example, by filtration, centrifugation, sedimentation, flocculation or other techniques known to the person skilled in the art.

Embodiments of the Invention

As mentioned above, the inventors of the present patent application surprisingly established, for the first time, a hydrophobic ionic exchange mixed-mode chromatography for the purification of enveloped viruses. This is a fully scalable and reproducible process. Said process allows the purification of enveloped viruses with high yield and purity. In addition, the inventors of the present patent application discovered that the presence of arginine in the elution buffer further allows to increase virus yield and purity. The recovery of high yield of enveloped viruses is extremely surprising as in the art arginine is used to inactivate enveloped viruses (EP2350271 B1). The method for virus purification of the present invention uses a mixed-mode chromatography in bind-elute-mode which is suitable to overcome actual shortcomings in the purification of enveloped viruses (e.g. in terms of purity, speed, recovery, universality, robustness and/or scalability). Said method is suitable to purify any enveloped virus from virus preparations. The obtained virus preparations fulfil the stringent guidelines of the regulatory authorities.

Thus, in a first aspect, the present invention relates to a method for purifying an enveloped virus comprising the steps of:
(i) binding an enveloped virus comprised in a preparation to a mixed mode chromatography carrier, and
(ii) eluting the enveloped virus from the mixed mode chromatography carrier,
wherein the mixed mode chromatography carrier is a hydrophobic ion exchange chromatography carrier.

The preparation comprising an enveloped virus in step (i) preferably comprises between $1\times10^7$ and $1\times10^{11}$ infectious viral particles (IVP)/ml.

Enveloped viruses associate unspecifically with cellular components and/or cell culture medium-related components. The accessible surface of enveloped viruses for this interaction is mainly the lipid membrane and the surface proteins embedded therein. For enveloped viruses, purification is especially difficult: the viral envelope may contain a highly complex and mobile collection of disparate molecules that range from sulfogroups in glycoproteins to aliphatic alcohols in sphingolipids that each or in combination present a range of electrostatic, van der Waals, or hydrophobic interaction surfaces for various binding partners derived from the culture medium itself, host cells, and/or other viral particles. The method of the present invention allows the reduction, in particular the removal, of said components from the preparation comprising an enveloped virus and, thus, the production of an enveloped virus having a high purity.

The preparation comprising an enveloped virus may be any composition containing an enveloped virus that is desired to be purified. It may be an impure, unpurified preparation (e.g. a cell suspension after virus culture or cell lysis) or a partially purified or pre-cleaned preparation (e.g. a clarified virus preparation). A partially purified preparation comes from an unpurified preparation that has been further processed (e.g. by at least one of filtration, centrifugation, flocculation, precipitation, sedimentation or alternative fractionation methods or by any combination thereof).

In particular, the preparation in step (i) refers to a composition comprising an enveloped virus that is desired to be purified from one or more contaminants. The one or more contaminants are preferably selected from the group consisting of viral substances (excluding the (intact) virus which is desired), non-viral intracellular substances, and/or non-viral extracellular substances, e.g. non-viral intracellular substances, or non-viral extracellular substances, or non-viral intracellular substances and non-viral extracellular substances, or non-viral intracellular substances, non-viral extracellular substances and viral substances (excluding the (intact) virus which is desired). Even more preferably, the viral substances are selected from the group consisting of incomplete virus particles and adventitious viruses, the non-viral intracellular substances are selected from the group consisting of cells, cellular debris, cellular remnants, cellular proteins, cellular lipids, and cellular nucleic acids, such as RNA and/or DNA molecules, and/or the non-viral extracellular substances are medium additives (used in cell cultivation and virus production).

A typical crude lysate of MVA virus-infected cells contains about $2.5\times10^5$ ng/ml DNA and about $3.0\times10^9$ pfu/ml MVA virus. Using $1\times10^8$ pfu as vaccine dose, one usually obtains 8300 ng of DNA per dose, more than 800-fold in excess of the amount of DNA admissible according to the WHO guideline. This DNA contamination as well as other contaminations are an enormous challenge that must be solved before vaccines from any continuous cell line can be produced and used in large scale, which is required for global vaccination against highly destructive infectious diseases. The preparation comprising an enveloped virus purified with the method of the present invention preferably comprises ≤40 ng nucleic acids/dose, e.g. 0,≤0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 ng nucleic acid/dose. The nucleic acids encompass DNA and/or RNA molecules.

In one embodiment, the preparation comprising an enveloped virus in step (i) is selected from the group consisting of a cell suspension comprising an enveloped virus, a cell lysate comprising an enveloped virus, and a clarified virus preparation comprising an enveloped virus. In one embodiment, the cell suspension, cell lysate, or clarified virus preparation are nuclease treated.

The skilled person knows how to produce a cell suspension comprising an enveloped virus. Usually, the cells are infected or transfected with the enveloped virus (host cells) and cultured over a defined period of time (cell culture). Usually, the infected cell suspensions are harvested after the infectious cycle has completed. For example, infectious virus titers for MVA peak 48 h after infection, can be harvested 72 h after infection and can then be further purified with the method of the present invention. Preferably, said virus producing cell in an uninfected or untransfected state is derived from a continuous cell line such as AGE1.CR, AGE1.CR.pIX, AGE1.HN, AGE1.R06E, AGE1.R05T, MDCK (Madin-Darby Canine Kidney; ATCC CCL 34), BHK (Baby Hamster Kidney) 21 (ATCC CCL-10), BHK TK (ECACC No. 85011423), HEK (Human Embryonic Kidney) 293 (ATCC CRL 1573), or DF-1 (chicken fibroblast cell line developed by Doug Foster). The cell line AGE1.CR.pIX (17a11b) was deposited by ProBioGen, Goethestr. 54, 13086 Berlin, Germany, with the DSMZ-Deutsche Sammlung von Mikroorganismen und Zellkulturen GmbH, Mascheroder Weg 1b, 38124 Braunschweig, Germany on Nov. 24, 2005 under accession number DSM ACC2749. The cell line AGE1.HN (NC5T11 #34) was deposited by ProBioGen, Goethestr. 54, 13086 Berlin, Germany, with the DSMZ-Deutsche Sammlung von Mikroorganismen und Zellkulturen GmbH, Mascheroder Weg 1b, 38124 Braunschweig, Germany on Nov. 4, 2005 under accession number DSM ACC2744. The cell line AGE1.R06E was deposited by ProBioGen, Goethestr. 54, 13086 Berlin, Germany, with the DSMZ-Deutsche Sammlung von Mikroorganismen und Zellkulturen GmbH, Inhoffenstr. 7B, 38124 Braunschweig, Germany on Apr. 3, 2008 under accession number DSM ACC2902.

Further, the skilled person knows how to produce a cell lysate comprising an enveloped virus from an enveloped virus producing cell (in a cell culture). For example, the cell lysate is produced by mechanical methods, e.g. ultrasound, temperature changes, blending or pressure homogenization through a narrow valve, or by chemical methods, e.g. with osmotic shock or detergents such as Tween-20 or Triton X-100.

The cell lysate is preferably produced by adding one or more chaotropic salts and/or polar or charged macromolecules to an enveloped virus producing cell prior to cell lysis, and lysing said enveloped virus producing cell. The chaotropic salts and/or polar or charged macromolecules bind to one or more of the non-viral substances, preferably intra- or extracellular substances, and/or said virus. The chaotropic salts and/or polar or charged macromolecules are masking compounds which protect binding sites that mediate association of virions with host cell factors or debris from downstream processing. Preferably, the chaotropic salts are NaBr and/or KCl and/or urea, optionally in combination with dextran sulphate and/or polyphosphoric acid and/or polyvinylpyrrolidon. Preferably, the concentration of the chaotropic salts and/or polar or charged macromolecules is such that the virus remains substantially intact and/or infectious. Substantially intact means that the half-life of the virus in serum, preferably human serum, is at least 10%, at least 20%, at least 30%, at least 40%, at least 50%, at least 60%, at least 70%, at least 80%, at least 90%, or at least 95% of the half-life of the virus not treated with the chaotropic salts and/or polar or charged macromolecules. More preferably, the concentration of NaBr is between 5 mM and 750 mM, between 25 mM and 700 mM, between 50 mM and 650 mM, between 75 mM and 600 mM, between 100 mM and 550 mM, between 125 mM and 500 mM, between 150 mM and 450 mM, between 175 mM and 400 mM, or preferably between 200 mM and 350 mM. Preferably, the pH is in the range of between 7.4 to 8.0, 6.0 to 6.5, 6.5 to 6.8, 6.8 to 7.2, more preferably 7.2 to 7.4. Preferably, the concentration of KCl is between 1 mM and 750 mM, between 15 mM and 700 mM, between 30 mM and 650 mM, between 45 mM and 600 mM, between 60 mM and 550 mM, between 75 mM and 500 mM, between 90 mM and 450 mM, between 105 mM and 400 mM, or preferably between 120 mM and 350 mM. Preferably, the concentration of urea is between 0.2 mM and 2 M, between 5 mM and 1 M, or between 100 mM and 500 mM. Preferably, the concentration of dextran sulfate is between 5 mg/l and 1000 mg/1, between 10 mg/l and 800 mg/l, or preferably between 15 mg/l and 600 mg/l. Preferably, the concentration of polyphosphoric acid is between 0.1 mM and 100 mM, between 0.2 mM and 80 mM, or preferably between 0.3 mM and 60 mM. Preferably, the concentration of polyvinylpyrrolidon is between 0.2% and 10%, between 1% and 8%, between 2% and 6% between 3% and 4%. Preferably, the concentration of Tween-20 and/or octylphenoxypolythoxyethanol (IGEPAL) is between 0.05% and 0.25%, between 0.1% and 0.20%, or preferably between 0.13% and 0.17%, each. Preferably, the pH is in the range of between 7.4 to 8.0, 6.0 to 6.5, 6.5 to 6.8, 6.8 to 7.2, more preferably 7.2 to 7.4.

Furthermore, the skilled person knows how to produce a clarified virus preparation comprising an enveloped virus. In particular, the enveloped virus can be separated from the cells and/or surrounding cell culture medium comprised in a cell suspension or from unlysed cells, cell debris, and/or surrounding medium in a cell lysate, e.g. by one or more of the following pre-purification/pre-treatment step(s): filtration, centrifugation, flocculation/precipitation, sedimentation or alternative fractionation methods, or any combination thereof. Only cell removal is, for example, required if the virus is released from the cells into the cell culture medium. If the cells have to be lysed first in order to release the virus, virus clarification starts with the cell lysate. In this case, the enveloped virus is separated from unlysed cells and cell debris, e.g. by one or more of the following pre-purification step(s): filtration, centrifugation, flocculation/precipitation, sedimentation or alternative fractionation methods, or any combination thereof.

In one another embodiment, the preparation comprising an enveloped virus in step (i) is subjected to one or more of the following (pre-treatment/pre-purification) steps selected from the group consisting of:

(a) cell lysis, (b) virus clarification, and (c) nuclease treatment prior to binding the enveloped virus to the mixed mode chromatography carrier.

Preferably, the preparation comprising an enveloped virus in step (i) is subjected to (b) virus clarification and optionally (c) nuclease treatment, or is subjected to (a) cell lysis, (b) virus clarification, and optionally (c) nuclease treatment prior to binding the enveloped virus to the mixed mode chromatography carrier.

For example, if the preparation comprising an enveloped virus is a cell suspension comprising an enveloped virus and the virus is released from the cell into the surrounding cell culture medium, virus clarification can directly be carried out. If the preparation comprising an enveloped virus is a cell suspension comprising an enveloped virus and the virus is not released from the cell into the surrounding cell culture medium, the cells have to be lysed first. Subsequently, virus clarification can be carried out.

The virus clarification step is preferably selected from the group consisting of chromatography, more preferably membrane adsorbers, filtration, more preferably dead-end filtration, depth filtration, membrane filtration, crossflow filtration, diafiltration (DF), ultrafiltration (UF), microfiltration (MF), or tangential flow depth filtration (TFDF), centrifugation, more preferably continuous flow centrifugation, discontinuous flow centrifugation, or density gradient centrifugation, flocculation/precipitation, more preferably through metal salts, macroporous materials or siliceous substances such as diatomaceous earth, cationic polymers such as Polyethylenglycol (PEG), Polyethlyenimine (PEI), Chitosan, or Polydiallyldimethylammoniumchlorid (pDADMAC), and sedimentation, more preferably through gravity forces.

As mentioned above, the method of the present invention overcomes actual shortcomings in the purification of enveloped viruses, e.g. in terms of purity, speed, recovery, robustness, and/or selectivity. The addition of a nuclease may further help to reduce the amount of nucleic acids, e.g. RNA and/or DNA molecules, in the virus preparation and, thus, may further increase purity.

Thus, in one embodiment, the preparation comprising an enveloped virus is prior to step (i) treated with a nuclease.

Prior to binding the enveloped virus comprised in the preparation to the mixed mode chromatography carrier, the preparation may further be precipitated, separated (e.g. by centrifugation in a density gradient or filtration), and/or loaded onto another chromatography column.

In one embodiment, the mixed mode chromatography carrier is equilibrated with an equilibration buffer, in particular prior to binding the enveloped virus to the mixed mode chromatography carrier. In this way, the chemical environment inside the carrier is equilibrated. The mixed mode carrier may be equilibrated to establish an appropriate pH, conductivity, and/or concentration of salts. Equilibration of the carrier is accomplished, for example, by flowing an equilibration buffer containing appropriate reagents though the column. The buffering compound may be Tris.

It might be useful when the preparation comprising an enveloped virus is re-buffered, concentrated, or diluted prior to binding the enveloped virus to the mixed mode chromatography carrier. For example, the preparation comprising an enveloped virus can be equilibrated to conditions compatible with the chromatography carrier equilibration buffer before applying the preparation to the chromatography carrier. The preparation may be equilibrated by adjusting the pH and/or the concentration of salts.

Alternatively, the mixed mode chromatography carrier in step (i) is an equilibrated mixed mode chromatography carrier and the preparation comprising an enveloped virus in step (i) is equilibrated to conditions compatible with the mixed mode chromatography carrier.

After the equilibration of the chromatography carrier and/or the preparation comprising an enveloped virus, the enveloped virus comprised in the preparation is bound to the chromatography carrier. The enveloped virus comprised in the preparation can be bound to the carrier at a linear flow velocity.

Following binding of the enveloped virus to the mixed mode chromatography carrier, the bound virus is optionally washed. Thus, in one embodiment, the method further comprises (after step (ii)) the step of:
(iii) washing the mixed mode chromatography carrier with a washing buffer, wherein the enveloped virus remains bound to the mixed mode chromatography carrier.

The washing step leads to the removal and/or displacement of the one or more contaminants, e.g. host cell proteins, host cell nucleic acids, such as DNA and/or RNA molecules, incomplete virus particles and/or adventitious viruses. More than one washing step, e.g. 2, 3, 4, or more washing steps, can be carried out.

Following the optional washing step, the enveloped virus is eluted from the mixed mode chromatography carrier. In one embodiment, the enveloped virus is eluted from the mixed mode chromatography carrier with an elution buffer. By eluting the enveloped virus from the mixed mode chromatography carrier, the enveloped virus is purified.

The equilibration buffer, washing buffer and elution buffer preferably comprise a salt and/or have a defined pH. The salt is preferably an alkali salt or alkaline earth salt. More preferably, the alkali salt is NaCl or KCl. Even more preferably, the alkali salt is NaCl. More preferably, the alkaline earth salt is $MgCl_2$.

In one preferred embodiment, the eluting in step (ii) is achieved using
an elution buffer having a higher salt concentration than the equilibration buffer and washing buffer,
an elution buffer having a higher pH than the equilibration buffer and washing buffer, or
an elution buffer having a higher salt concentration and a higher pH than the equilibration buffer and washing buffer.

In one another preferred embodiment, the equilibration buffer, washing buffer and elution buffer comprise a salt and/or have a defined pH, and the eluting in step (ii) comprises raising the salt concentration of the elution buffer (in contact with the enveloped virus bound to the mixed mode chromatography carrier) compared to the salt concentration of the equilibration buffer and washing buffer,
raising the pH of the elution buffer (in contact with the enveloped virus bound to the mixed mode chromatography carrier) compared to the pH of the equilibration buffer and washing buffer, or
raising the salt concentration and the pH of the elution buffer (in contact with the enveloped virus bound to the mixed mode chromatography carrier) compared to the salt concentration and pH of the equilibration buffer and washing buffer.

The eluted enveloped virus is highly concentrated as compared to the enveloped virus comprised in the preparation in step (i).

Preferably, the equilibration buffer comprises ≤0.8 M NaCl, e.g. 0,≤0.01, 0.05, 0.1, 0.2, 0.3, 0.4, 0.5, 0.6, 0.7, or 0.8 M NaCl, and/or has a pH of between about 7.0 and about 7.5, e.g. 7.0, 7.1, 7.2, 7.3, 7.4, or 7.5. More preferably, the equilibration buffer comprises between 0.01 M and 0.8 M NaCl, between 0.1 M and 0.8 M NaCl, or between 0.3 M and 0.6 M NaCl, Even more preferably, the equilibration buffer comprises between 0.3 M and 0.6 M NaCl.

Preferably, the washing buffer comprises ≤0.8 M NaCl, e.g. 0,≤0.01, 0.05, 0.1, 0.2, 0.3, 0.4, 0.5, 0.6, 0.7, or 0.8 M NaCl, and/or has a pH of between about 7.0 and about 7.5, e.g. 7.0, 7.1, 7.2, 7.3, 7.4, or 7.5. More preferably, the washing buffer comprises between 0.01 M and 0.8 M NaCl, between 0.1 M and 0.8 M NaCl, or between 0.3 M and 0.6 M NaCl. Even more preferably, the washing buffer comprises between 0.3 M and 0.6 M NaCl.

Preferably, the elution buffer comprises between 0.01 M and 3.0 M NaCl, e.g. 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 M NaCl, and/or has a pH of between about 7.0 and about 8.0, e.g. 7.1, 7.2, 7.3, 7.4, 7.5, 7.6, 7.7, 7.8, 7.9, or 8.0. More preferably, the elution buffer comprises between 0.2 M and 3.0 M NaCl. Even more preferably, the elution buffer comprises between 0.2 M and 2.0 M NaCl or between 0.5 and 2.0 M NaCl.

Most preferably,
the equilibration buffer and washing buffer comprise ≤0.5 M NaCl, e.g. 0.5 M NaCl, and have a pH of between about 7.0 and about 7.5, e.g. 7.2, and
the elution buffer comprises between ≥0.5 M and 3.0 M NaCl, e.g. 0.5 M NaCl or 2.0 M NaCl, and has a pH of between about 7.0 and about 8.0, e.g. 7.2.

The inventors of the present patent application surprisingly found that the presence of arginine in the elution buffer further allows to increase virus yield and purity. The recovery of high yield of enveloped viruses is extremely surprising as in the art arginine is used to inactivate enveloped viruses (EP2350271 B1). Thus, it is particularly preferred that the elution buffer comprises arginine. More preferably, the elution buffer comprises between 0.2 M and 1.0 M arginine, e.g. 0.2, 0.25, 0.3, 0.4, 0.5, 0.6, 0.7, 0.75, 0.8, 0.9, or 1.0 M arginine. Even more preferably, the elution buffer comprises between 0.01 M and 3.0 M NaCl, e.g. 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 M NaCl, and between 0.2 M and 1.0 M arginine, e.g. 0.2, 0.25, 0.3, 0.4, 0.5, 0.6, 0.7, 0.75, 0.8, 0.9, or 1.0 M arginine, and/or has a pH of between 7.0 and 8.0, e.g. 7.0, 7.1, 7.2, 7.3, 7.4, 7.5, 7.6, 7.7, 7.8, 7.9, or 8.0.

In one particularly preferred embodiment, the elution buffer comprises between >1.0 M and 3.0 M NaCl, preferably 2.0 M NaCl, e.g. 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 M NaCl, and between 0.2 and ≤0.5 M arginine, preferably 0.25 M arginine, e.g. 0.2, 0.25, 0.3, 0.4, 0.5 M arginine (high salt buffer).

In one another particularly preferred embodiment, the elution buffer comprises between 0.01 M and 1.0 M NaCl, preferably 0.5 M NaCl, e.g. 0.01, 0.05, 0.1, 0.2, 0.3, 0.4, 0.5, 0.6, 0.7, 0.8, 0.9, 1.0 M NaCl, and between >0.5 M and 1.0 M arginine, preferably 0.75 M arginine, e.g. 0.6, 0.7, 0.75, 0.8, 0.9, or 1.0 M arginine (low salt buffer).

The pH of the above elution buffers is preferably between 7.0 and 8.0, e.g. 7.0, 7.1, 7.2, 7.3, 7.4, 7.5, 7.6, 7.7, 7.8, 7.9, or 8.0.

Preferably, the preparation comprising an enveloped virus in step (i) comprises ≤0.8 M NaCl, e.g. 0,≤0.01, 0.05, 0.1, 0.2, 0.3, 0.4, 0.5, 0.6, 0.7, or 0.8 M NaCl, and/or has a pH of between about 7.0 and about 7.5, e.g. 7.0, 7.1, 7.2, 7.3, 7.4, or 7.5, when bound to the mixed mode chromatography carrier. Said preparation comprising an enveloped virus preferably comprises between $1\times10^7$ and $1\times10^{12}$ infectious viral particles (IVP)/ml.

The mixed-mode chromatography carrier, in particular the hydrophobic ion exchange chromatography carrier, is operated in a bind-elute mode. Especially, the enveloped virus is eluted by changing buffer conditions (e.g. salt and/or pH-value and/or arginine concentration such as (i) salt concentration, (ii) pH value, (iii) arginine concentration, (iv) salt concentration and pH-value, (v) salt and arginine concentration, (vi) pH value and arginine concentration, or (vii) salt concentration, pH-value and arginine concentration). By eluting the enveloped virus from the mixed mode chromatography carrier in step (ii), a mixed mode eluate is formed.

The eluate may directly be mixed with a virus formulation buffer or subjected to one or more post-treatment/post-purification steps to prepare the virus for virus formulation.

In one embodiment, the eluate is further subjected to one or more of the following (post-treatment/post-purification) steps selected from the group consisting of:
(a) filtration, preferably dead-end filtration, depth filtration, membrane filtration, crossflow filtration, diafiltration (DF), ultrafiltration (UF), microfiltration (MF), or tangential flow depth filtration (TFDF),
(b) chromatography, preferably size exclusion chromatography, affinity chromatography, pseudo-affinity chromatography, gel filtration chromatography, or membrane adsorbers, and
(c) nuclease treatment.

In one preferred embodiment, the mixed mode eluate is treated with a nuclease. In this case, the nuclease is preferably directly added to the eluate without buffer exchange. Preferably, the nuclease is a salt active nuclease such as SAN High Quality™ (ArcticZymes). The nuclease treatment may be performed in a solution/suspension containing ≥1.0 M NaCl, e.g. 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, or 3.0 M NaCl. The nuclease is used to digest cellular nucleic acids, such as RNA and/or DNA molecules, and, thus, contributes to enveloped virus purification. It was surprising for the present inventors that the nuclease was effective outside the described range of ≤1.0 M NaCl, i.e. >1.0 M NaCl. The recommended salt concentration is usually 0.5 M NaCl with some activity preserved at 1.0 M NaCl. The nuclease was surprisingly also effective in an eluate/a solution/a buffer containing ≤1.0 M NaCl and >0.5 M arginine.

Thus, in one preferred embodiment, the nuclease is added to an eluate comprising between >1.0 M and 3.0 M NaCl, preferably 2.0 M NaCl, e.g. 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 M NaCl, and between 0.2 and ≤0.5 M arginine, preferably 0.25 M arginine, e.g. 0.2, 0.25, 0.3, 0.4, 0.5 M arginine.

In one another preferred embodiment, the nuclease is added to an eluate comprising between 0.01 M and 1.0 M NaCl, preferably 0.5 M NaCl, e.g. 0.01, 0.05, 0.1, 0.2, 0.3, 0.4, 0.5, 0.6, 0.7, 0.8, 0.9, 1.0 M NaCl, and between >0.5 M and 1.0 M arginine, preferably 0.75 M arginine, e.g. 0.6, 0.7, 0.75, 0.8, 0.9, or 1.0 M arginine (low salt buffer).

The pH of the above eluates is preferably between 7.0 and 8.0, e.g. 7.0, 7.1, 7.2, 7.3, 7.4, 7.5, 7.6, 7.7, 7.8, 7.9, or 8.0.

It is also preferred that the nuclease treatment is performed in a solution/buffer comprising arginine, e.g. after buffer exchange. More preferably, the solution/buffer comprises between 0.2 and 1.0 M arginine, e.g. 0.2, 0.3, 0.4, 0.5, 0.6, 0.7, 0.8, 0.9, or 1.0 M arginine. Even more preferably, the solution/buffer also comprises between 0.01 M and 3.0 M NaCl, e.g. 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 M NaCl, and between 0.2 and 1.0 M arginine, e.g. 0.2, 0.3, 0.4, 0.5, 0.6, 0.7, 0.8, 0.9, or 1.0 M arginine. and/or has a pH of between 7.0 and 8.0, e.g. 7.0, 7.1, 7.2, 7.3, 7.4, 7.5, 7.6, 7.7, 7.8, 7.9, or 8.0.

Preferably the nuclease is subsequently removed from the eluate, e.g. via chromatography, more preferably via size exclusion chromatography, affinity chromatography, pseudo-affinity chromatography, gel filtration chromatography, or membrane adsorbers, and/or via filtration, more preferably via dead-end filtration, depth filtration, membrane filtration, crossflow filtration, diafiltration (DF), ultrafiltration (UF), microfiltration (MF), or tangential flow depth filtration (TFDF).

In one embodiment, the mixed mode eluate is mixed with a formulation buffer. A final filtration step may subsequently be conducted (see FIG. 1).

As mentioned above, the enveloped virus is bound to a mixed mode chromatography carrier in step (i). The mixed mode chromatography carrier is a hydrophobic ion exchange chromatography carrier. The use of a hydrophobic ion exchange chromatography carrier for the purification of preparations comprising enveloped viruses allows to obtain enveloped viruses with high purity, potency, and quality that meet the stringent guidelines of the regulatory authorities. In one embodiment, the hydrophobic ion exchange chromatography carrier is a hydrophobic cationic exchange chromatography carrier or a hydrophobic anion exchange chromatography carrier, preferably a hydrophobic cationic exchange chromatography carrier. Preferably, the hydrophobic cationic exchange chromatography carrier comprises a ligand comprising at least one hydrophobic and at least one acidic moiety. More preferably, the hydrophobic moiety is a phenyl ring or an aliphatic hydrocarbon chain, and/or the acidic moiety is a carboxyl group. Even more preferably, the ligand is a p-aminohippuric acid. The carrier is preferably packed in a column. The carrier may also be a membrane or resin. Commercially available examples of a hydrophobic cation exchange carrier include, but are not limited to, Capto MMC™ (available from GE Healthcare) and Nuvia™ cPrime™ (available from Bio-Rad).

An exemplarily method for purifying an enveloped virus may have the following steps:
(i) optionally cell lysis,
(ii) virus clarification, e.g. filtration or centrifugation,
(iii) hydrophobic ion exchange chromatography (e.g. with binding step, optionally washing step, and eluting step), and
(iv) optionally nuclease treatment and subsequent nuclease removal, e.g. by chromatography or tangential flow filtration (TFF).

In particular, the method for purifying an enveloped virus may have the following steps:
(i) cell lysis,
(ii) virus clarification, e.g. filtration or centrifugation,
(iii) hydrophobic ion exchange chromatography (e.g. with binding step, optionally washing step, and eluting step), and
(iv) nuclease treatment and subsequent nuclease removal, e.g. by chromatography or tangential flow filtration (TFF).

In one preferred embodiment, the method for purifying an enveloped virus comprises the steps of:

(i) binding an enveloped virus comprised in a preparation to a mixed mode chromatography carrier, wherein the mixed mode chromatography carrier is a hydrophobic ion exchange chromatography carrier,
(ii) eluting the enveloped virus from the mixed mode chromatography carrier with an elution buffer comprising between >1.0 M and 3.0 M NaCl, preferably 2.0 M NaCl, e.g. 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 M NaCl (high salt buffer), thereby forming an eluate, and
(iii) optionally adding a nuclease to the eluate.

In one more preferred embodiment, the method for purifying an enveloped virus comprises the steps of:
(i) binding an enveloped virus comprised in a preparation to a mixed mode chromatography carrier, wherein the mixed mode chromatography carrier is a hydrophobic ion exchange chromatography carrier,
(ii) eluting the enveloped virus from the mixed mode chromatography carrier with an elution buffer comprising between >1.0 M and 3.0 M NaCl, preferably 2.0 M NaCl, e.g. 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 M NaCl, and between 0.2 and ≤0.5 M arginine, preferably 0.25 M arginine, e.g. 0.2, 0.25, 0.3, 0.4, 0.5 M arginine (high salt buffer), thereby forming an eluate, and
(iii) optionally adding a nuclease to the eluate.

In one even more preferred embodiment, the method for purifying an enveloped virus comprises the steps of:
(i) binding an enveloped virus comprised in a preparation to a mixed mode chromatography carrier, wherein the mixed mode chromatography carrier is a hydrophobic ion exchange chromatography carrier,
(ii) eluting the enveloped virus from the mixed mode chromatography carrier with an elution buffer comprising between 0.01 M and 1.0 M NaCl, preferably 0.5 M NaCl, e.g. 0.01, 0.05, 0.1, 0.2, 0.3, 0.4, 0.5, 0.6, 0.7, 0.8, 0.9, 1.0 M NaCl, and between >0.5 M and 1.0 M arginine, preferably 0.75 M arginine, e.g. 0.6, 0.7, 0.75, 0.8, 0.9, or 1.0 M arginine (low salt buffer), thereby forming an eluate, and
(iii) optionally adding a nuclease to the eluate.

Preferably the nuclease is subsequently removed from the eluate, e.g. via chromatography, more preferably via size exclusion chromatography, affinity chromatography, pseudo-affinity chromatography, gel filtration chromatography, or membrane adsorbers, and/or via filtration, more preferably via dead-end filtration, depth filtration, membrane filtration, crossflow filtration, diafiltration (DF), ultrafiltration (UF), microfiltration (MF), or tangential flow depth filtration (TFDF).

It is preferred that the enveloped virus is a live enveloped virus, an attenuated enveloped virus, or a replication deficient enveloped virus. It is (alternatively or additionally) preferred that the enveloped virus is a wild-type enveloped virus, recombinant enveloped virus, or modified enveloped virus.

It is more preferred that the enveloped virus is
a negative-sense single stranded RNA ((−) ssRNA) virus,
a positive-sense single stranded RNA ((+) ssRNA) virus,
a double stranded DNA (dsDNA) virus, or
a reverse transcribing virus.

It is even more preferred that
the negative-sense single stranded RNA ((−) ssRNA) virus is a virus of the Orthomyxoviridae, Paramyxoviridae, Arenaviridae, Bornaviridae, Bunyaviridae, Filoviridae, or Rhabdoviridae family, or a Hepatitis-D-virus,
the positive-sense single stranded RNA ((+) ssRNA) virus is a virus of the Flaviviridae, Coronaviridae, or Togaviridae family,
the double stranded DNA (dsDNA) virus is a virus of the Poxviridae, Herpesviridae, or Hepadnaviridae family, or
the reverse transcribing virus is a virus of the Retroviridae family It is most preferred that
the virus of the Orthomyxoviridae family is selected from the group consisting of influenza A virus, influenza B virus, influenza C virus, Isavirus, Quaranjavirus, and Thogotovirus,
the virus of the Paramyxoviridae family is selected from the group consisting of Newcastle disease (ND) virus, Sendai virus, measles virus, Hendra virus, and Nipah virus,
the virus of the Flaviviridae family is selected from the group consisting of Flavivirus, Pegivirus, and Pestivirus,
the virus of the Coronaviridae family is a porcine epidemic diarrhea virus (PEDV),
wherein the virus of the Retroviridae family is an alpha, a beta, gamma, or delta retrovirus, a lentivirus, or a spumavirus, or
the virus of the Poxviridae family is a vaccinia virus, preferably a Modified Vaccinia Ankara (MVA) virus, more preferably a recombinant Modified Vaccinia Ankara (MVA) virus.

In preferred embodiments, the enveloped virus is a Modified Vaccinia Ankara (MVA) virus (see examples).

It is particularly preferred that the enveloped virus further comprises a heterologous nucleic acid sequence. Said heterologous nucleic acid sequence is preferably selected from the group consisting of a sequence coding for an antigen, particularly an epitope of an antigen, a diagnostic compound, and a therapeutic compound.

In a second aspect, the present invention relates to an enveloped virus or a plurality of enveloped viruses obtainable by the method of the first aspect. The enveloped virus is preferably substantially free of contaminants, e.g. viral substances (excluding the virus which is desired), non-viral intracellular substances, and/or non-viral extracellular substances. The viral substances are preferably selected from the group consisting of incomplete virus particles and adventitious viruses, the non-viral intracellular substances are preferably selected from the group consisting of cells, cellular debris, cellular remnants, cellular proteins, cellular lipids, and cellular nucleic acids, and/or the non-viral extracellular substances are preferably medium additives (used in cell cultivation and virus production). In particular, the enveloped virus or the plurality of enveloped viruses comprises ≤40 ng nucleic acids/dose, e.g. 0,≤0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 ng nucleic acid/dose. The nucleic acids may be DNA and/or RNA molecules. The enveloped virus or plurality of enveloped viruses may be comprised in a formulation buffer.

In a third aspect, the present invention relates to the enveloped virus or the plurality of enveloped viruses of the second aspect for use in medicine.

It is preferred to use the enveloped virus or the plurality of enveloped viruses of the second aspect for gene therapy, e.g. in order to introduce a therapeutic gene, or to modify or correct an endogenous gene. The therapeutic gene may be introduced into a mammal, e.g. human or the endogenous gene may be modified or corrected within the mammal, e.g. human.

It is also preferred to use the enveloped virus or the plurality of enveloped viruses of the second aspect as vaccine/for vaccination, in particular to induce an immune response, e.g. in a mammal such as human.

It is further preferred to use the enveloped virus or the plurality of enveloped viruses of the second aspect for preventing or treating a disease, e.g. an inherited or an acquired disease, an infection, or cancer.

In a fourth aspect, the present invention relates to an elution buffer comprising arginine. Preferably, the elution buffer comprises between 0.2 to 1.0 M arginine, e.g. 0.2, 0.25, 0.3, 0.4, 0.5, 0.6, 0.7, 0.75, 0.8, 0.9, or 1.0 M arginine. In particular, the elution buffer has a pH of between 7.0 and 8.0, e.g. 7.0, 7.1, 7.2, 7.3, 7.4, 7.5, 7.6, 7.7, 7.8, 7.9, or 8.0. More preferably, the elution buffer comprises between 0.01 M and 3.0 M NaCl, e.g. 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 M NaCl, and between 0.2 to 1.0 M arginine, e.g. 0.1, 0.2, 0.25, 0.3, 0.4, 0.5, 0.6, 0.7, 0.75, 0.8, 0.9, or 1.0 M arginine, and/or has a pH of between 7.0 and 8.0, e.g. 7.0, 7.1, 7.2, 7.3, 7.4, 7.5, 7.6, 7.7, 7.8, 7.9, or 8.0. For further preferred ranges, it is referred to the first aspect of the present invention.

In a fifth aspect, the prevent invention relates to the use of a buffer comprising arginine to elute an enveloped virus. Preferably, the elution buffer comprises between 0.2 to 1.0 M arginine, e.g. 0.2, 0.25, 0.3, 0.4, 0.5, 0.6, 0.7, 0.75, 0.8, 0.9, or 1.0 M arginine. In particular, the elution buffer has a pH of between 7.0 and 8.0, e.g. 7.0, 7.1, 7.2, 7.3, 7.4, 7.5, 7.6, 7.7, 7.8, 7.9, or 8.0.

More preferably, the elution buffer comprises between 0.01 M and 3.0 M NaCl, e.g. 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 M NaCl, and between 0.2 to 1.0 M arginine, e.g. 0.1, 0.2, 0.25, 0.3, 0.4, 0.5, 0.6, 0.7, 0.75, 0.8, 0.9, or 1.0 M arginine, and/or has a pH of between 7.0 and 8.0, e.g. 7.0, 7.1, 7.2, 7.3, 7.4, 7.5, 7.6, 7.7, 7.8, 7.9, or 8.0. For further preferred ranges, it is referred to the first aspect of the present invention.

In a further aspect, the present invention relates to the use of arginine and a nuclease or to the use of arginine in combination with a nuclease to purify an enveloped virus. The arginine is preferably comprised in a buffer. In particular, the buffer comprises between 0.2 to 1.0 M arginine, e.g. 0.2, 0.25, 0.3, 0.4, 0.5, 0.6, 0.7, 0.75, 0.8, 0.9, or 1.0 M arginine. In particular, the buffer has a pH of between 7.0 and 8.0, e.g. 7.0, 7.1, 7.2, 7.3, 7.4, 7.5, 7.6, 7.7, 7.8, 7.9, or 8.0. More preferably, the buffer comprises between 0.01 M and 3.0 M NaCl, e.g. 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 M NaCl, and between 0.2 to 1.0 M arginine, e.g. 0.1, 0.2, 0.25, 0.3, 0.4, 0.5, 0.6, 0.7, 0.75, 0.8, 0.9, or 1.0 M arginine, and/or has a pH of between 7.0 and 8.0, e.g. 7.0, 7.1, 7.2, 7.3, 7.4, 7.5, 7.6, 7.7, 7.8, 7.9, or 8.0. For further preferred ranges, it is referred to the first aspect of the present invention. As to the nuclease, it is also referred to the first aspect of the present invention.

In a sixth aspect, the present invention relates to a kit for purifying an enveloped virus comprising:
(i) a mixed mode chromatography carrier, wherein the mixed mode chromatography carrier is a hydrophobic ion exchange chromatography carrier,
(ii) one or more of the following buffers: equilibration buffer, washing buffer, and elution buffer, and
(iii) optionally a nuclease.

In one embodiment, the kit comprises an equilibration buffer, a washing buffer, and an elution buffer. In one preferred embodiment, the kit comprises an elution buffer and optionally an equilibration buffer and/or a washing buffer. Preferably, the elution buffer comprises arginine. More preferably, the elution buffer comprises between 0.2 to 1.0 M arginine, e.g. 0.2, 0.25, 0.3, 0.4, 0.5, 0.6, 0.7, 0.75, 0.8, 0.9, or 1.0 M arginine. In particular, the elution buffer has a pH of between 7.0 and 8.0, e.g. 7.0, 7.1, 7.2, 7.3, 7.4, 7.5, 7.6, 7.7, 7.8, 7.9, or 8.0.

Even more preferably, the elution buffer comprises between 0.01 M and 3.0 M NaCl, e.g. 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 M NaCl, and between 0.2 to 1.0 M arginine, e.g. 0.1, 0.2, 0.25, 0.3, 0.4, 0.5, 0.6, 0.7, 0.75, 0.8, 0.9, or 1.0 M arginine, and/or has a pH of between 7.0 and 8.0, e.g. 7.0, 7.1, 7.2, 7.3, 7.4, 7.5, 7.6, 7.7, 7.8, 7.9, or 8.0. For further preferred ranges, it is referred to the first aspect of the present invention.

In one more preferred embodiment, the kit further comprises a nuclease. As to the nuclease which is optionally present, it is also referred to the first aspect of the present invention. The kit is useful to purify an enveloped virus. In particular, the kit is useful to carry out the method according to the first aspect.

The kit may further comprise instructions (e.g. on a data carrier such as CD-ROM or DVD) on how to carry out enveloped virus purification as well as packaging material.

The present invention is summarized as follows:

1. A method for purifying an enveloped virus comprising the steps of:
   (i) binding an enveloped virus comprised in a preparation to a mixed mode chromatography carrier, and
   (ii) eluting the enveloped virus from the mixed mode chromatography carrier,
   wherein the mixed mode chromatography carrier is a hydrophobic ion exchange chromatography carrier.
2. The method of item 1, wherein the preparation comprising an enveloped virus in step
   (i) is subjected to one or more of the following steps selected from the group consisting of:
   (a) cell lysis,
   (b) virus clarification, and
   (c) nuclease treatment
   prior to binding the enveloped virus to the mixed mode chromatography carrier.
3. The method of item 2, wherein the virus clarification step is selected from the group consisting of chromatography, filtration, centrifugation, flocculation/precipitation, and sedimentation.
4. The method of any one of items 1 to 3, wherein the mixed mode chromatography carrier is equilibrated with an equilibration buffer.
5. The method of any one of items 1 to 4, wherein the method further comprises the step of:
   (iii) washing the mixed mode chromatography carrier with a washing buffer, wherein the enveloped virus remains bound to the mixed mode chromatography carrier.
6. The method of any one of items 1 to 5, wherein the enveloped virus is eluted from the mixed mode chromatography carrier with an elution buffer.
7. The method of any one of items 4 to 6, wherein the eluting in step (ii) is achieved using an elution buffer having a higher salt concentration than the equilibration buffer and washing buffer, an elution buffer having a higher pH than the equilibration buffer and washing buffer, or
an elution buffer having a higher salt concentration and a higher pH than the equilibration buffer and washing buffer.
8. The method of any one of items 4 to 6, wherein the equilibration buffer, washing buffer and elution buffer comprise a salt and/or have a defined pH, and wherein the eluting in step (ii) comprises
raising the salt concentration of the elution buffer compared to the salt concentration of the equilibration buffer and washing buffer,
raising the pH of the elution buffer compared to the pH of the equilibration buffer and washing buffer, or
raising the salt concentration and the pH of the elution buffer compared to the salt concentration and pH of the equilibration buffer and washing buffer.
9. The method of any one of items 4 to 8, wherein the equilibration buffer comprises ≤0.8 M NaCl and/or has a pH of between 7.0 and 7.5.
10. The method of any one of items 5 to 9, wherein the washing buffer comprises ≤0.8 M NaCl and/or has a pH of between 7.0 and 7.5.
11. The method of any one of items 6 or 10, wherein the elution buffer comprises between 0.2 M and 3.0 M NaCl and/or has a pH of between 7.0 and 8.0.
12. The method of any one of items 4 to 11, wherein
the equilibration buffer and washing buffer comprise ≤0.5 M NaCl, preferably 0.5 M NaCl, and have a pH of between 7.0 and 7.5, preferably 7.2, and
the elution buffer comprises between ≥0.5 M and 3.0 M NaCl, preferably 2.0 M NaCl, and has a pH of between 7.0 and 8.0, preferably 7.2.
13. The method of any one of items 6 to 12, wherein the elution buffer comprises arginine.
14. The method of item 13, wherein the elution buffer comprises between 0.2 and 1.0 M arginine.
15. The method of items 13 or 14, wherein the elution buffer comprises between 0.2 M and 3.0 M NaCl and between 0.2 to 1.0 M arginine, and/or has a pH of between 7.0 and 8.0.
16. The method of any one of items 1 to 15, wherein the preparation comprising an enveloped virus in step (i) comprises ≤0.8 M NaCl and/or has a pH of between 7.0 and 7.5 when bound to the mixed mode chromatography carrier.
17. The method of any one of items 1 to 16, wherein by eluting the enveloped virus from the mixed mode chromatography carrier in step (ii), a mixed mode eluate is formed.
18. The method of item 17, wherein the eluate is further subjected to one or more of the following steps selected from the group consisting of:
(a) filtration,
(b) chromatography, and
(c) nuclease treatment.
19. The method of items 17 or 18, wherein the mixed mode eluate is treated with a nuclease.
20. The method of items 18 or 19, wherein the nuclease is subsequently removed from the eluate via chromatography, preferably size exclusion chromatography, and/or filtration, preferably via tangential flow filtration (TFF), ultrafiltration (UF), diafiltration (DF), gelfiltration, or a combination of gelfiltration and tangential flow filtration (TFF).
21. The method of any one of items 17 to 20, wherein the mixed mode eluate is mixed with a formulation buffer.
22. The method of any one of items 1 to 21, wherein the hydrophobic ion exchange chromatography carrier is a hydrophobic cationic exchange chromatography carrier or a hydrophobic anion exchange chromatography carrier, preferably a hydrophobic cationic exchange chromatography carrier.
23. The method of item 22, wherein the hydrophobic cationic exchange chromatography carrier comprises a ligand comprising at least one hydrophobic and at least one acidic moiety.
24. The method of item 23, wherein the hydrophobic moiety is a phenyl ring or an aliphatic hydrocarbon chain, and/or wherein the acidic moiety is a carboxyl group.
25. The method of items 23 or 24, wherein the ligand is a p-aminohippuric acid.
26. The method of any one of items 1 to 25, wherein the carrier is packed in a column.
27. The method of any one of items 1 to 26, wherein the preparation comprising an enveloped virus in step (i) comprises one or more contaminants selected from the group consisting of viral substances, non-viral intracellular substances, and/or non-viral extracellular substances.
28. The method of item 27, wherein
the viral substances are selected from the group consisting of incomplete virus particles and adventitious viruses,
the non-viral intracellular substances are selected from the group consisting of cells, cellular debris, cellular remnants, cellular proteins, cellular lipids, and cellular nucleic acids, and/or
the non-viral extracellular substances are medium additives (used in cell cultivation and virus production).
29. The method of any one of items 1 to 28, wherein the enveloped virus is a live enveloped virus, an attenuated enveloped virus, or a replication deficient enveloped virus.
30. The method of any one of items 1 to 29, wherein the enveloped virus is a wild-type enveloped virus, recombinant enveloped virus, or modified enveloped virus.
31. The method of any one of items 1 to 30, wherein the enveloped virus is
a negative-sense single stranded RNA ((−) ssRNA) virus,
a positive-sense single stranded RNA ((+) ssRNA) virus,
a double stranded DNA (dsDNA) virus, or
a reverse transcribing virus.
32. The method of item 31, wherein
the negative-sense single stranded RNA ((−) ssRNA) virus is a virus of the Orthomyxoviridae, Paramyxoviridae, Arenaviridae, Bornaviridae, Bunyaviridae, Filoviridae, or Rhabdoviridae family, or a Hepatitis-D-virus,
the positive-sense single stranded RNA ((+) ssRNA) virus is a virus of the Flaviviridae, Coronaviridae, or Togaviridae family,
the double stranded DNA (dsDNA) virus is a virus of the Poxviridae, Herpesviridae, or Hepadnaviridae family, or
the reverse transcribing virus is a virus of the Retroviridae family
33. The method of item 32, wherein
the virus of the Orthomyxoviridae family is selected from the group consisting of influenza A virus, influenza B virus, influenza C virus, Isavirus, Quaranjavirus, and Thogotovirus, the virus of the Paramyxoviridae family is selected from the group consisting of Newcastle disease (ND) virus, Sendai virus, measles virus, Hendra virus, and Nipah virus, the virus of the Flaviviridae family is selected from the group consisting of Flavivirus, Pegivirus, and Pestivirus, the virus of the Coronaviridae family is a porcine epidemic diarrhea virus (PEDV), the virus of the Retroviridae family is an alpha, a beta, gamma, or delta retrovirus, a lentivirus, or a spumavirus, or the virus of the Poxviridae family is a vaccinia virus, preferably a Modified Vaccinia Ankara (MVA) virus.

34. The method of any one of items 1 to 33, wherein the enveloped virus further comprises a heterologous nucleic acid sequence.

35. The method of item 34, wherein the heterologous nucleic acid sequence is selected from the group consisting of a sequence coding for an antigen, particularly an epitope of an antigen, a diagnostic compound, and a therapeutic compound.

36. An enveloped virus or a plurality of enveloped viruses obtainable by the method of any one of items 1 to 35.

37. The enveloped virus or the plurality of enveloped viruses of item 36 for use in medicine.

38. An elution buffer comprising arginine.

39. Use of a buffer comprising arginine to elute an enveloped virus.

40. A kit for purifying an enveloped virus comprising:
   (i) a mixed mode chromatography carrier, wherein the mixed mode chromatography carrier is a hydrophobic ion exchange chromatography carrier,
   (ii) one or more of the following buffers: equilibration buffer, washing buffer, and elution buffer, and
   (iii) optionally a nuclease.

41. The kit of item 40, wherein the elution buffer comprises arginine.

42. The kit of items 40 or 41, wherein the kit is useful to purify an enveloped virus.

43. The kit of any one of items 40 to 42, wherein the kit comprises instructions on how to carry out enveloped virus purification.

Various modifications and variations of the invention will be apparent to those skilled in the art without departing from the scope of invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art in the relevant fields are intended to be covered by the present invention.

BRIEF DESCRIPTION OF THE FIGURES

The following Figures and examples are merely illustrative of the present invention and should not be construed to limit the scope of the invention as indicated by the appended claims in any way.

EXAMPLES

Figure 1:
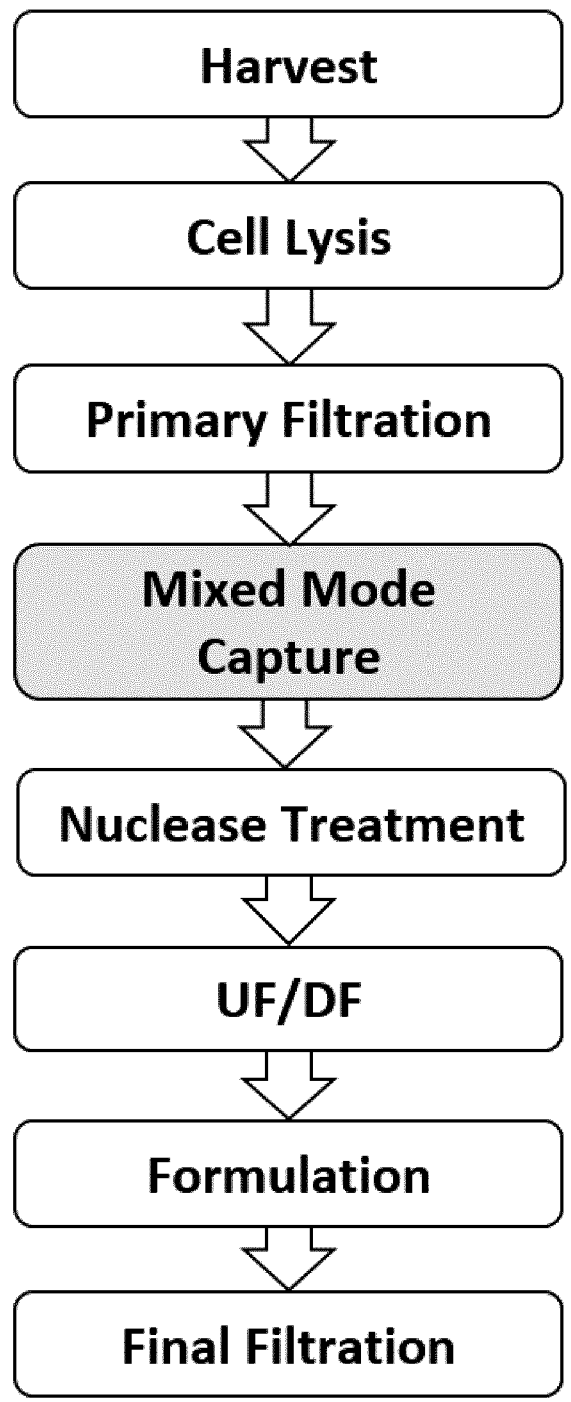
FIG. 1: Schematic presentation of an exemplarily method of enveloped virus purification according to the present invention.

The examples given below are for illustrative purposes only and do not limit the invention described above in any way.

Example 1

Modified Vaccinia Ankara (MVA) Virus Production

MVA-CR19.gfp, a fluorescent version of the parental MVA-CR19 clone (U.S. Pat. No. 9,732,325 B2), was produced in AGE1.CR.pIX cells (Jordan I, Vos A, Beilfuss S, Neubert A, Breul S, Sandig V. An avian cell line designed for production of highly attenuated viruses. Vaccine. 2009; 7:748-756) cultivated in growth medium until a viable cell density of $2 \times 10^6$ cells/ml. For virus production, 50% of the growth medium CD-U4 (GE Healthcare, USA) was replaced by CD-VP4 medium (Gibco, USA) to induce cellular aggregates supporting virus spread. Cells were infected with a multiplicity of infection (MOI) of 0.005 and cultured for up to three days before harvest. Cells were not separated from culture supernatant but lysed directly using ultrasound. Titers of 10^9/ml or above were regularly obtained in this process.

Example 2

MVA Virus Titration (TCID50, qTCID50)

Virus titration of MVA was performed on adherent AGE1.CR.pIX for both methods TCID50 and qTCID50. For the TCID50 (Tissue Culture Infection Dose 50) assay, 96-well plates were infected 24 h after seeding $2.5 \times 10^5$ cells/ml in DMEM/F12 (Gibco, USA) containing 5% FCS by serial virus dilutions. The evaluation was 48 h after the incubation at 37° C. and calculated according to Reed and Muench (Reed L J, Muench H. A simple method of estimating fifty per cent endpoints. Am J Hyg 1938; 27: 493-497). Furthermore qTCID50, the titer determination by quantitative polymerase chain reaction (qPCR), for MVA was developed and established. Similarly to TCID50 the cell-plates were infected by the defined standard diluted $10^{-2}$-$10^{-6}$ and the samples diluted $10^{-3}$. After the incubation for 6 h the medium was removed and the wells were washed with PBS. For cell lysis 50 µl per well QuickExtract DNA Extraction Solution 1.0 (Epicentre, USA) was used and the plate heated to 65° C. for 15 min, following by an incubation step at 95° C. for 5 min. After adding 100 µl WFI, the samples were used for qPCR. To 15 µl of the final mastermix which contains the primer pair MVA128L 5'-CGTTTTG-CATCATACCTCCATCTT-3' (SEQ ID NO: 1) and 5'-GCGGGTGCTGGAGTGCTT-3' (SEQ ID NO: 2), TIB MolBiol, Germany), Power SYBR Green PCR Master Mix (Thermo Fisher Scientific, USA) and WFI 5 µl probe was added each. For the non-template control (NTC) WFI was used. The qPCR was performed in a StepOnePlus RealTime PCR System (Applied Biosystems, USA) programmed to 95° C. for 10 min followed by 40 cycles of denaturation at 95° C. for 15 s and annealing and DNA amplification at 60° C. for 1 min. The evaluation was based on the ct-values and the titer of the MVA standard.

Example 3

MVA Virus Purification via Mixed Mode Chromatography

At harvest, part of the virus can be found in the supernatant, however, the majority of the virus remains inside cells. Although the virus fraction in the supernatant is higher for MVA-CR19 (U.S. Pat. No. 9,732,325 B2), the intracellular fraction is still important and cell lysis is preferably included into the process. For release of intracellular MVA virus, cells in production medium were incubated with chaotropic salts (250 mM NaBr, 250 mM NaCl, and/or 150 mM KCl, see U.S. Pat. No. 9,273,289 B2) to detach host cell DNA from virus particles and lysed using ultrasound (amplitude 10%, 45 s).

Primary clearance of the lysate was performed with prefilters (Sartopure, Sartorius, Germany) to remove cellular debris and larger particles that might cause challenges in the following purification steps (FIG. 1).

Already after this stage, nuclease treatment can be applied to reduce host cell DNA. However, precipitates were observed in lysates treated with nuclease, requiring an additional filtration step as a prerequisite to chromatography. This step removed more than 50%, sometimes even 80% of the virus. Moreover, at the high volume of the cleared lysate nuclease treatment is not economic. Therefore, although nuclease treatment can be performed at this stage which would ease removal of nuclease in the following steps, it is preferred to omit nuclease treatment at this stage but to perform it after chromatography instead.

Figure 2:
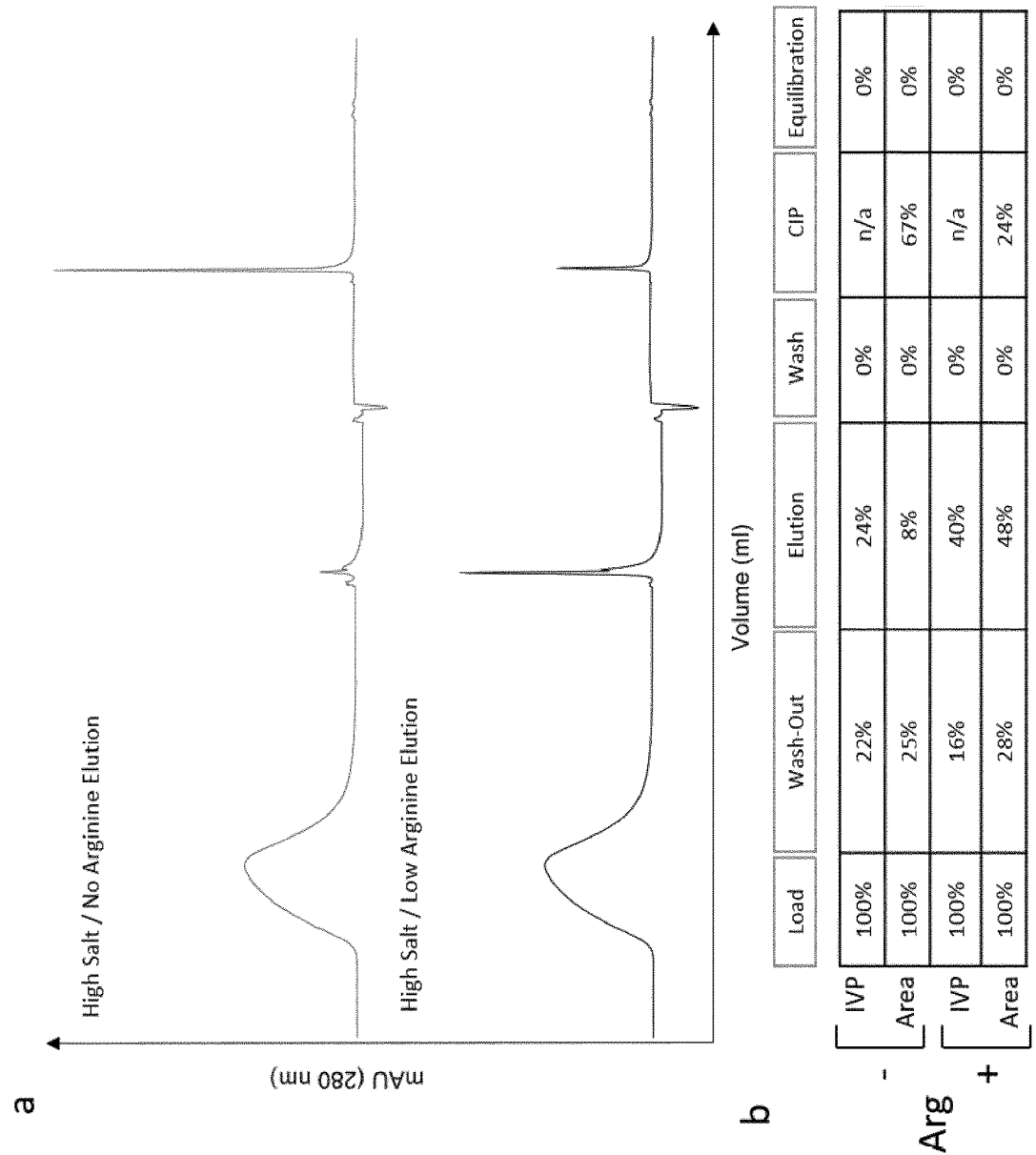
FIG. 2: Effect of Arginine during elution from a mixed mode medium. (a) Representative chromatogram of virus capture and recovery under indicated conditions. Virus lysate was loaded to the mixed mode resin, washed and finally eluted by applying either buffer supplied with 2 M NaCl only (grey) or elution buffer containing 2 M NaCl and 0.25 M Arginine (black). b) Typical recoveries of infectious particles (IVP) and Peak areas during the individual chromatography steps shown in a) in absence or presence of arginine (+/−Arg) in the elution buffer.

The central component for virus purification is an efficient capture step allowing in parallel reduction of harvest volumes, concentration of virus and removal of major contaminants early during downstream purification. Due to their various modes of binding interactions, mixed mode carriers were anticipated to be particularly suitable for enveloped viruses with their inhomogeneous structure, lipid and protein composition as well as their heterogeneous surface charges. Moreover, mixed mode carriers were considered applicable to various viruses as a platform step. However, the typical conditions binding to and eluting from mixed mode carriers may cause inactivation of fragile enveloped viruses. Mixed mode carrier compatible for large scale production have recently become commercially available through various vendors but have not been used for enveloped viruses. By screening different mixed mode ligands, capture of MVA for a number of ligands under conditions compatible with viable virus was indeed observed. Most efficient capture was achieved efficient with mixed mode cation exchangers Capto MMC™ (available from GE Healthcare) and Nuvia™ cPrime™ (available from Bio-Rad) under the applied conditions (pH 7.2±0.2, 55 mS/cm) as judged by substantial reduction of infectious units in the flow through fraction (FIG. 2).

For a preferred process, $5 \times 10^9$ infectious virus particles were loaded per ml of resin (Nuvia cPrime, Biorad, Germany) equilibrated with 50 mM Tris, 0.5 M NaCl, pH 7.2. Contaminants were washed out with 25 CV of Wash buffer (50 mM Tris, 0.5 M NaCl, pH 7.2) as evident by the increase in UV absorption (FIG. 2a).

To release viral particles from the mixed mode carrier, increasing the salt concentration in the elution buffer was tested. Elution with 50 mM Tris. HCL and 2 M NaCl allowed to recover about 24% of infectious virus, whereas the residual bound material was released during CIP (FIG. 2b). Interestingly, virus recoveries were significantly improved from 24% to about 40% when arginine was added to the elution buffer and the CIP peak area diminished accordingly (FIG. 2a, b)

It is, therefore, preferred to elute virus with an elution buffer containing 50 mM Tris.HCL, 2 M NaCl, and 250 mM arginine, pH 7.2. Considering the negative impact of arginine on viruses, this finding is surprising. Notably, the eluted material was relieved from about 97.5% of contaminating cellular DNA (Table 1) as well as about 98% of protein contaminants and, thus, can be designated as substantially purified when compared to the initial material applied to the carrier.

Figure 3:
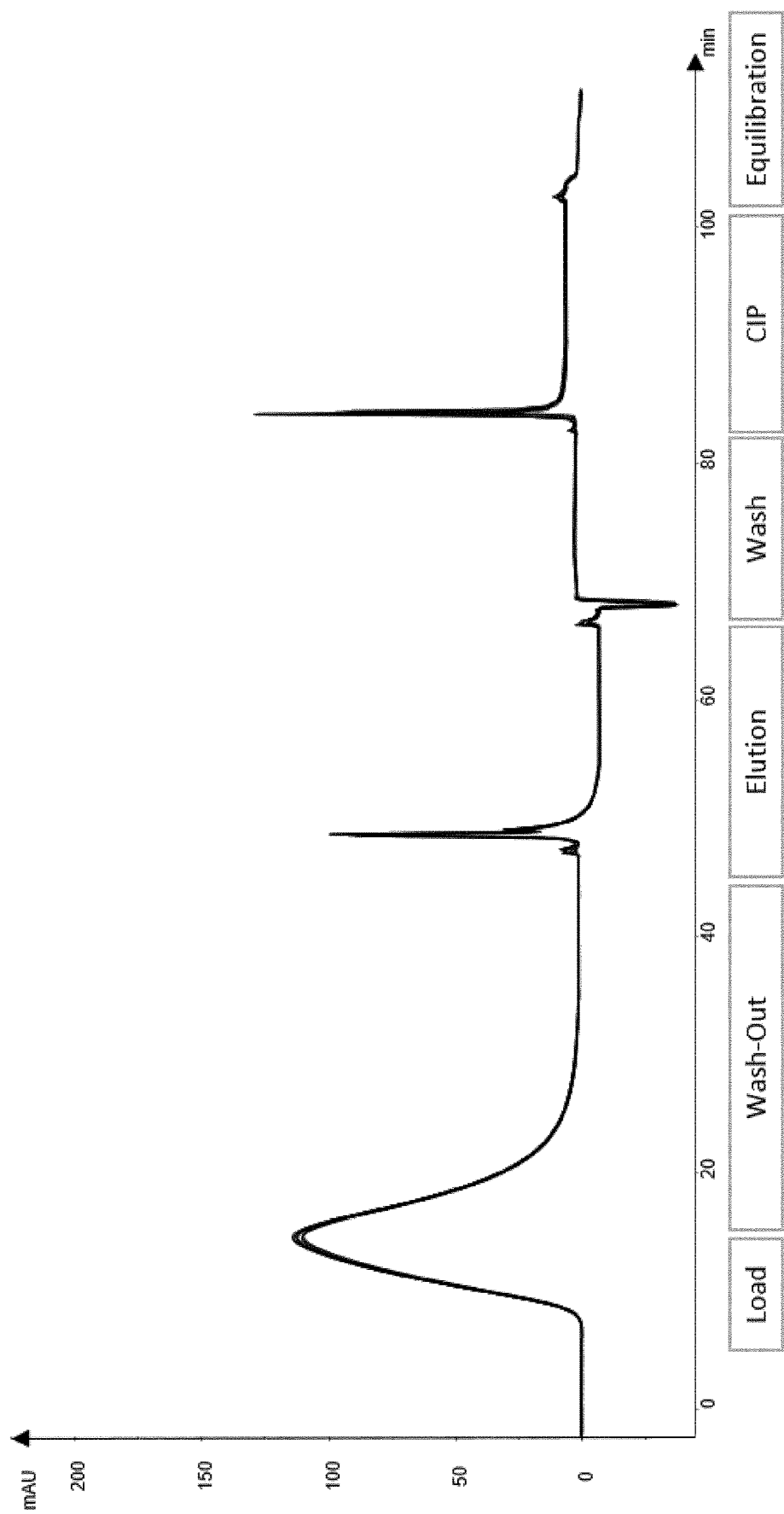
FIG. 3: Reproducibility of virus capture using a mixed mode medium. Overlay of successive chromatography runs (n=10) performed on the same mixed mode resin under optimised conditions demonstrates the robustness of virus capture through the described method. In each step, optimised amounts of virus lysates from the primary clarification step were loaded, washed and finally recovered using elution buffer supplied with 2 M NaCl and 0.25 M arginine.

Consistency of virus capture using the mixed mode ligand was examined by successive runs on the same mixed mode carrier using an elution buffer containing arginine. As shown in FIG. 3, virus capture and elution could be reproducibly performed with the method described here, even at extended use of the carrier (n=10). Besides demonstration of process robustness, this finding has major impact on the column size required for scale-up and suggests that the process described here is not restricted by such issues.

Example 4

Reduction of DNA by Nuclease Treatment and Removal of Nuclease

To further reduce cellular DNA burden and meet the requirement for human vaccines/therapeutic products, another chromatography might be considered but nuclease treatment might be the most appropriate step. However, the high salt concentration in the eluate might be not compatible with the activity of many nucleases. To digest, DNA buffer can be exchanged by TFF to reduce the salt concentration, an additional step that will reduce overall yield. Alternatively, a nuclease active in higher salt concentration such as SAN (Artic Enzymes, Norway) may be used. The recommended salt concentration for this nuclease is 500 mM with, some activity preserved at 1M. Surprisingly, an 150 fold reduction of DNA per virus dose was found when the partially purified material/eluate was treated with 50 U/ml of SAN overnight at room temperature.

After digestion, nuclease can be removed either by tangential flow filtration or by using a gel filtration carrier separating the enzyme from the virus particles due to size differences. Diafiltration against elution buffer using hollow fibers (750 kDa mPES, SpectrumLabs, USA) and mild shear rates (500 1/s) removed nuclease with a step yield of 98%. The same step is applied to change buffer to a suitable formulation for application.

TABLE 1

Representative virus yields and DNA levels during purification of recombinant MVA using an elution buffer containing 2M NaCl and 250 mM Arginine (examples 3 and 4). Cell lysis and primary filtration were performed as described in example 3. Nuvia cPrime was loaded with 5 × 10⁹ IVP/ml resin. Contaminants were washed out with 25 CV of Wash buffer (50 mM Tris, 0.5M NaCl, pH 7.2) and bound virus eluted with 5 CV of Elution buffer (50 mM Tris.HCL, 2M NaCl, 250 mM Arginine, pH 7.2). The partially purified material/eluate was further treated with a nuclease as described in example 4.

| Purification step | IVP Yield (Step) | IVP Yield (Overall) | DNA Reduction (Step) | DNA Reduction (Overall) | DNA/ Dose* [ng] |
|---|---|---|---|---|---|
| Cell Lysis | 100% | 100% | 0% | 0.00% | 1200 |
| Primary Filtration | 95% | 95% | 20% | 20.00% | 960 |
| Capture | 40% | 38% | 97% | 97.5% | 30 |
| Nuclease | 90% | 34% | 99% | 99.98% | 0.2 |

*Based on calculations considering 1 × 10⁸ IVP/dose

Example 5

Mixed Mode Chromatography at High Arginine Concentration

It is desired to lower the salt concentration in the elution step to facilitate nuclease digestion without prior buffer exchange. Since it was observed that the addition of arginine improves virus recovery, it was reasoned that a very high arginine concentration could substitute for NaCl.

Figure 4:
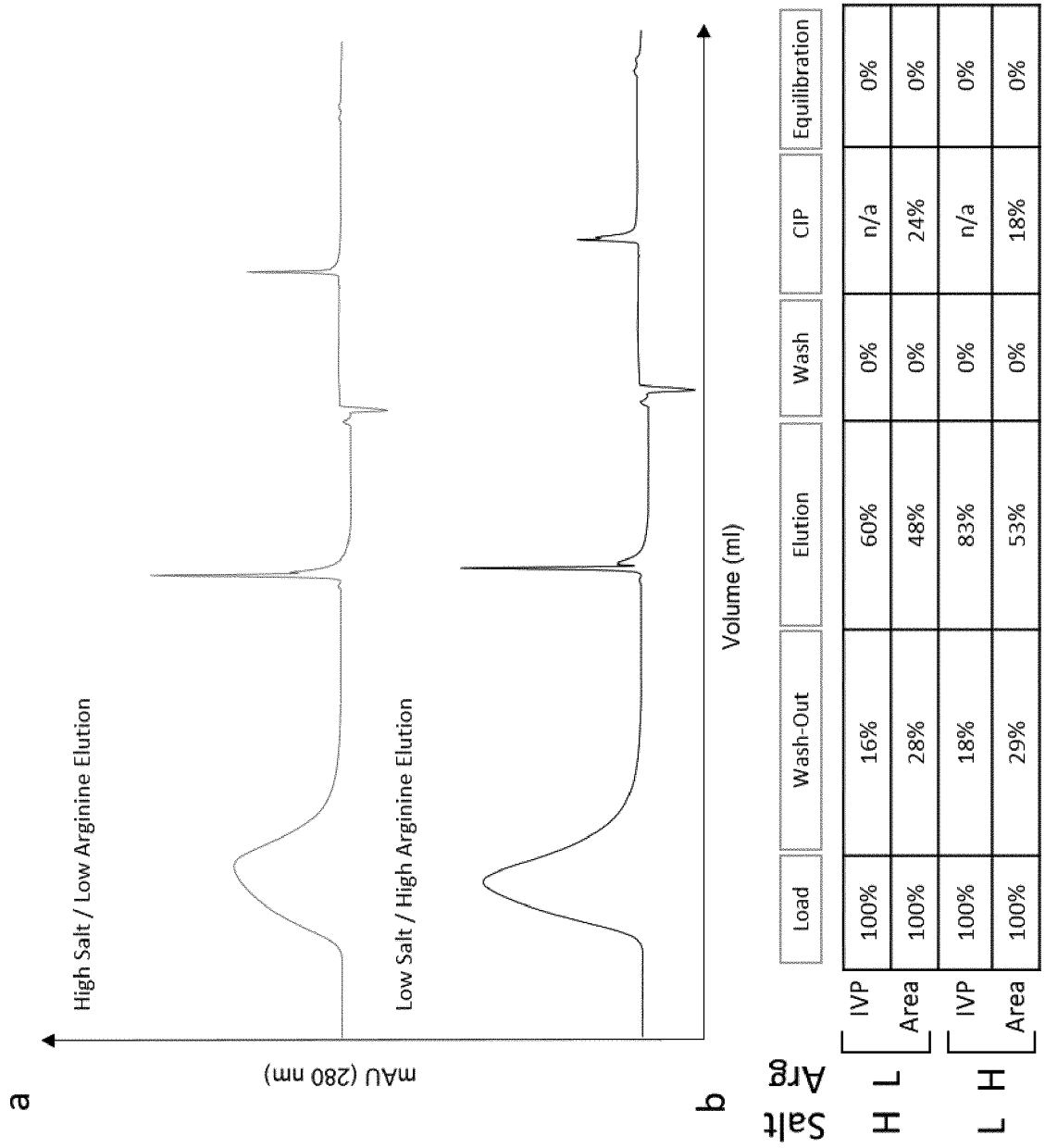
FIG. 4: High arginine concentrations can substitute high salt requirements during elution and allow further improved virus recoveries from a mixed mode carrier. a) Representative chromatogram of virus capture and recovery under indicated conditions. Virus lysate was loaded to the mixed mode resin, washed and finally eluted by applying buffer supplied either with 2 M NaCl and 0.25 M Arginine (grey) or elution buffer containing 0.5 M NaCl and 0.75 M Arginine (black). b) Typical recoveries of infectious particles (IVP) and Peak areas during the individual chromatography steps shown in a) in absence or presence of arginine (+/−Arg) in the elution buffer.

Lysate was prepared, pretreated and applied to the chromatography resin (Nuvia cPrime, Biorad, Germany) as described in example 3. Contaminants were washed out with 25 CV of Wash buffer (50 mM Tris, 0.5 M NaCl, pH 7.2). For the elution buffer, arginine concentration was raised threefold (0.75 M) and the salt concentration was decreased fourfold (0.5 M). Due to this approach, virus recoveries were further improved to about 83% (FIG. 4a, b).

The eluate was subjected to nuclease treatment without prior buffer exchange. DNA content was reduced more than 500× by treatment with 50 U/ml of SAN overnight at room temperature. Consequently, SAN nuclease has higher activity at 500 mM NaCl as expected but was also insensitive to high concentrations 750 mM of arginine. The overall process yield and purity is described in Table 2.

TABLE 2

Representative virus yields and DNA levels during purification of recombinant MVA using an elution buffer containing 0.5M NaCl and 750 mM Arginine (example 5). Cells lysis and primary filtration were performed as described in example 3. Nuvia cPrime was loaded with 5 × 10⁹ IVP/ml resin. Contaminants were washed out with 25 CV of Wash buffer (50 mM Tris, 0.5M NaCl, pH 7.2) and bound virus eluted with 5 CV of Elution buffer (50 mM Tris.HCL, 0.5M NaCl, 750 mM Arginine, pH 7.2). The partially purified material was further treated with a nuclease as described in example 5.

| Purification step | IVP Yield (Step) | IVP Yield (Overall) | DNA Reduction (Step) | DNA Reduction (Overall) | DNA/ Dose* [ng] |
|---|---|---|---|---|---|
| Cell Lysis | 100% | 100% | 0% | 0.00% | 1200 |
| Primary Filtration | 95% | 95% | 20% | 20.00% | 960 |
| Capture | 83% | 79% | 97% | 97.3% | 33 |
| Nuclease | 100% | 79% | 100% | 100.00% | 0.06 |

*Based on calculations considering 1 × 10⁸ IVP/dose

Example 6

Quantitation of Host Cell DNA

The measurement of purified samples with a low amount of DNA was performed by qPCR. Before DNA extraction the samples with high salt levels were diluted $10^{-1}$ and the defined standard $10^{-1}$-$10^{-6}$. To 5 µl QuickExtract DNA Extraction Solution 1.0 (Epicentre, USA) 20 µl sample was added and heated to 65° C. and incubate for 15 min, following by an incubation step at 95° C. for 5 min using a C1000 Touch Thermal Cycler (Bio Rad, USA). Afterwards 50 µl of WFI were added. The qPCR method and the composition of the mastermix were identical to the one used for the qTCID50 except for the primer pair duPseudo2 (5'-CAGGCAGGTTTCTTTAGGAAGG-3' (SEQ ID NO: 3) and 5'-GTAGGTAGCAAGGAGGTTTAGC-3' (SEQ ID NO: 4), (TIB MolBiol, Germany).

Example 7

Newcastle Disease Virus (NDV) Production

Newcastle disease virus (NDV) was produced in AGE1.CR.pIX cells. Suspension cultures were maintained in a shaking incubator (HT Multitron Cell, Infors AG, Bottmingen, Switzerland) on a rotating platform with amplitude of 5 cm and rotation speed of 180 $min^{-1}$. $CO_2$ atmosphere was set to 8% and temperature to 37° C. All culture vessels, shake tubes (Tubespin 50, TPP Techno Plastic Products AG, Switzerland) or baffled shake flasks (Corning, NY, USA), were equipped with 0.2 µm filtered lids to allow gas exchange. Culture volumes were maintained at 20-50% of the vessel size.

The DASBox (DASGip, Eppendorf, Hamburg, Germany) bioreactor units were equipped with a Marine impeller with three blades and 60-250 ml working-volume vessels. Gas mixing was performed with $N_2$, air, $CO_2$ and $O_2$, pH was adjusted with $CO_2$ and 1 M $Na_2CO_3$. Inoculation was usually performed to 1×10⁶ cells/ml in CD-U3 medium and the culture was allowed to proliferate for 3 days to approximately 4×10⁶ cells/ml. The parameters for the cell proliferation phase were 37° C. culture temperature, 60% DO (dissolved oxygen) saturation in the medium, 180 rpm for the impeller, and a pH gradient that decreased from 7.25 to 7.00 units in the cell culture during cell proliferation. The pH was usually kept at 7.1 units during infection.

Propagation of NDV virus was furthermore supported by feeding recombinant trypsin (rTrypsin, Novozym 6395020) into the infected culture from a solution kept at 4° C. with an activity adjusted such that a feeding rate of 0.17 ml/h (4 ml per day) resulted in a final concentration of 8 U/ml of culture volume each day. The incubation temperature was set to 35° C.

Example 8

Newcastle Disease Virus Purification via Mixed Mode Chromatography

The cell suspension was subjected to three freeze-thaw cycles and cell debris was removed by filtration (Sartopure, Sartorius, Germany) as described for the MVA process. The obtained material was subjected to a chromatography step using a mixed mode cation exchanger (Nuvia cPrime, Biorad, Germany) Contaminants were washed out with 25 CV of Wash buffer and bound virus eluted with 5 CV of Elution buffer and live virus was recovered.

The partially purified material/eluate was further treated with 50 U/ml of nuclease (SAN, Artic Enzymes, Norway) overnight at room temperature.

The enzyme as well as DNA fragments and smaller impurities were removed by diafiltration against Elution buffer using hollow fibers.

Example 9

Determination of Infectious Units

Infectious titres of Newcastle disease virus (NDV) were determined on Vero cells. $1.5 \times 10^6$ cells in DMEM:F12 medium containing 2 mM GlutaMAX I (both Gibco) and 5% foetal calf serum (Biochrom) were seeded into Cell-BIND 96-well plates (Corning) at 100 µl of cell suspension. The medium was replaced on the following day against DMEM:F12 containing 2 mM GlutaMAX I and 1.5 µg/ml trypsin (type IX-S, Sigma T0303), but no foetal calf serum. Serial dilutions in steps of 10 of NDV samples were prepared in DMEM:F12 medium free of serum, and 10 µl each of the dilutions were added to the Vero cultures. Virus replication was allowed at 37° C. for 72 h.

Detection of NDV replication was facilitated by immunostaining: the cells were fixed in methanol for 10 min, allowed to dry to completion, and rehydrated with PBS containing 0.05% Tween-20. NDV antiserum (GD Animal Health Deventer, the Netherlands) was added to a dilution of 1:2000 in PBS containing 1% foetal calf serum and incubated for 1 h at room temperature. After two washes with PBS, secondary antibody (anti-chicken, Alexa Fluor 488 labelled, host rabbit, Dianova, 303-545-003 at 1 µg/µl) was added at a dilution of 1:2000 for 2 h at ambient temperature or overnight at 4° C. Infected wells were identified by fluorescence after two washes with PBS. Calculation of TCID50 values was performed according to Reed et al. (Reed L J, Muench H. A simple method of estimating fifty per cent endpoints. Am J Hyg 1938; 27: 493-497).

---

The invention claimed is:

1. A method for purifying an enveloped virus comprising the steps of:
   (i) binding an enveloped virus comprised in a preparation to a mixed mode chromatography carrier, and
   (ii) eluting the enveloped virus from the mixed mode chromatography carrier with an elution buffer, wherein the mixed mode chromatography carrier is a hydrophobic ion exchange chromatography carrier and wherein the elution buffer comprises arginine.

2. The method of claim 1, wherein the preparation comprising an enveloped virus in step (i) is subjected to one or more of the following steps selected from the group consisting of:
   (a) cell lysis,
   (b) virus clarification, and
   (c) nuclease treatment
   prior to binding the enveloped virus to the mixed mode chromatography carrier.

3. The method of claim 1, wherein the mixed mode chromatography carrier is equilibrated with an equilibration buffer.

4. The method of claim 1, wherein the method further comprises the step of:
   (iii) washing the mixed mode chromatography carrier with a washing buffer, wherein the enveloped virus remains bound to the mixed mode chromatography carrier.

5. The method of claim 3, wherein the eluting in step (ii) is achieved using
   an elution buffer having a higher salt concentration than the equilibration buffer and washing buffer,
   an elution buffer having a higher pH than the equilibration buffer and washing buffer, or
   an elution buffer having a higher salt concentration and a higher pH than the equilibration buffer and washing buffer.

6. The method of claim 1, wherein by eluting the enveloped virus from the mixed mode chromatography carrier in step (ii), a mixed mode eluate is formed.

7. The method of claim 6, wherein the eluate is further subjected to one or more of the following steps selected from the group consisting of:
   (a) filtration,
   (b) chromatography, and
   (c) nuclease treatment.

* * * * *

SEQUENCE LISTING

<160> NUMBER OF SEQ ID NOS: 4

<210> SEQ ID NO 1
<211> LENGTH: 24
<212> TYPE: DNA
<213> ORGANISM: artificial
<220> FEATURE:
<223> OTHER INFORMATION: synthetic
<220> FEATURE:
<221> NAME/KEY: primer
<222> LOCATION: (1)..(24)

<400> SEQUENCE: 1
cgttttgcat catacctcca tctt                                    24

<210> SEQ ID NO 2
<211> LENGTH: 18
<212> TYPE: DNA
<213> ORGANISM: artificial
<220> FEATURE:
<223> OTHER INFORMATION: synthetic
<220> FEATURE:
<221> NAME/KEY: primer
<222> LOCATION: (1)..(18)

<400> SEQUENCE: 2
gcgggtgctg gagtgctt                                           18

<210> SEQ ID NO 3
<211> LENGTH: 22
<212> TYPE: DNA
<213> ORGANISM: artificial
<220> FEATURE:
<223> OTHER INFORMATION: synthetic
<220> FEATURE:

```
<221> NAME/KEY: primer
<222> LOCATION: (1)..(22)

<400> SEQUENCE: 3
caggcaggtt tctttaggaa gg                                              22

<210> SEQ ID NO 4
<211> LENGTH: 22
<212> TYPE: DNA
<213> ORGANISM: artificial
<220> FEATURE:
<223> OTHER INFORMATION: synthetic
<220> FEATURE:
<221> NAME/KEY: primer
<222> LOCATION: (1)..(22)

<400> SEQUENCE: 4
gtaggtagca aggaggttta gc                                              22
```